United States Patent
Nüesch et al.

(10) Patent No.: US 9,029,117 B2
(45) Date of Patent: May 12, 2015

(54) MODIFIED RODENT PARVOVIRUS CAPABLE OF PROPAGATING AND SPREADING THROUGH HUMAN GLIOMAS

(75) Inventors: Jürg Nüesch, Heidelberg (DE); Nadja Thomas, Siessen (DE); Claudia Plotzky, Ilvesheim (DE); Jean Rommelaere, Heidelberg (DE)

(73) Assignee: Deutsches Krebsforschungzentrum, Heidelberg (DE)

( * ) Notice: Subject to any disclaimer, the term of this patent is extended or adjusted under 35 U.S.C. 154(b) by 0 days.

(21) Appl. No.: 13/696,373

(22) PCT Filed: May 9, 2011

(86) PCT No.: PCT/EP2011/002306
§ 371 (c)(1),
(2), (4) Date: Dec. 12, 2012

(87) PCT Pub. No.: WO2011/138053
PCT Pub. Date: Nov. 10, 2011

(65) Prior Publication Data
US 2013/0129683 A1 May 23, 2013

(30) Foreign Application Priority Data
May 7, 2010 (EP) .................................. 10004897

(51) Int. Cl.
*C12N 7/00* (2006.01)
*C12N 15/00* (2006.01)
*C07H 21/04* (2006.01)
*C12N 7/02* (2006.01)
*C07K 14/005* (2006.01)

(52) U.S. Cl.
CPC ................ *C12N 7/02* (2013.01); *C07K 14/005* (2013.01); *C12N 7/00* (2013.01); *C12N 2750/14322* (2013.01); *C12N 2750/14332* (2013.01); *C12N 2750/14343* (2013.01); *A61K 35/768* (2013.01)

(58) Field of Classification Search
CPC .................. C07K 14/005; C12N 2750/14321; C12N 7/00; C12N 2770/36122; C12N 2770/36143; C12N 2770/10022; C12N 2740/16222; C12N 2750/14322; C12N 2750/14332; C12N 2760/16121; C12N 2760/16122; C12N 2760/16132; A61K 38/162; A61K 2039/525
See application file for complete search history.

(56) References Cited

U.S. PATENT DOCUMENTS

| 4,159,319 | A | 6/1979 | Bachmann et al. |
| 2004/0220124 | A1 | 11/2004 | Rommelaere et al. |

FOREIGN PATENT DOCUMENTS

| EP | 0496135 A2 | 7/1992 |
| JP | 64566620 A | 3/1989 |
| WO | WO 00/57907 A2 | 10/2000 |

OTHER PUBLICATIONS

Zhi et al. Molecular and Functional Analyses of a Human Parvovirus B19 Infectious Clone Demonstrates Essential Roles for NS1, VP1 and the 11-Kilodalton Protein in Virus Infectivity. Journal of Virology, 2006. 80(12): 5941-5950.*
International Search Report mailed Jan. 23, 2012 for the corresponding PCT Application No. PCT/EP2011/002306.
Written Opinion of the International Searching Authority mailed Nov. 7, 2012 for the corresponding PCT Application No. PCT/EP2011/002306.
International Preliminary Report on Patentability mailed Nov. 13, 2012 for the corresponding PCT Application No. PCT/EP2011/002306.
Calle et al, Parvovirus H-1 infection of human glioma cells leads to complete viral replication and efficient cell killing, *International Journal of Cancer*, 2004, pp. 76-84, vol. 109, No. 1.
Bar et al, Vesicular egress of non-enveloped lytic parvoviruses depends on gelsolin functioning, *PLOS Pathogens*, 2008, pp. E1000126, vol. 4, No. 8.
Qiu et al., Parvovirus RNA processing strategies, *Parvoviruses*, pp. 253-274, 2006.
Rhode et al., Parvovirus Genome: Nucleotide Sequence of H-1 and Mapping of Its Genes by Hybrid-Arrested Translation, *Journal of Virology*, 1983, pp. 173-184, vol. 45, No. 1.
Kohler et al., Continuous cultures of fused cells secreting antibody of predefined specificity, *Nature*, Aug. 1975, pp. 495-497.
Galfre et al., Preparation of monoclonal antibodies: strategies and procedures, *Methods in Enzymol*, 1981, pp. 3-46, vol. 73.
Di Piazza et al., Cytosolic activation of cathepsins mediates parvovirus H-1-induced killing of cisplatin and TRAIL-resistant glioma cells, *Jounal of Virology*, Apr. 2007, pp. 4186-4198.

* cited by examiner

*Primary Examiner* — Maria Leavitt
*Assistant Examiner* — Kimberly A Aron
(74) *Attorney, Agent, or Firm* — Leason Ellis LLP.

(57) ABSTRACT

Described are (a) parvovirus variants capable of propagating and spreading through human tumor cells which is obtainable by serially passaging a rodent parvovirus as starting strain in semi-permissive human tumor cells, and (b) parvovirus variants capable of propagating and spreading through human tumor cells characterized by particular amino acid deletions and/or substitutions, e.g. a deletion of several amino acids in the C-terminus of NS1/middle exon of NS2. A pharmaceutical composition containing such parvoviruses as well as their use for the treatment of cancer, preferably a glioblastoma, is also described.

33 Claims, 14 Drawing Sheets

Figure 2:
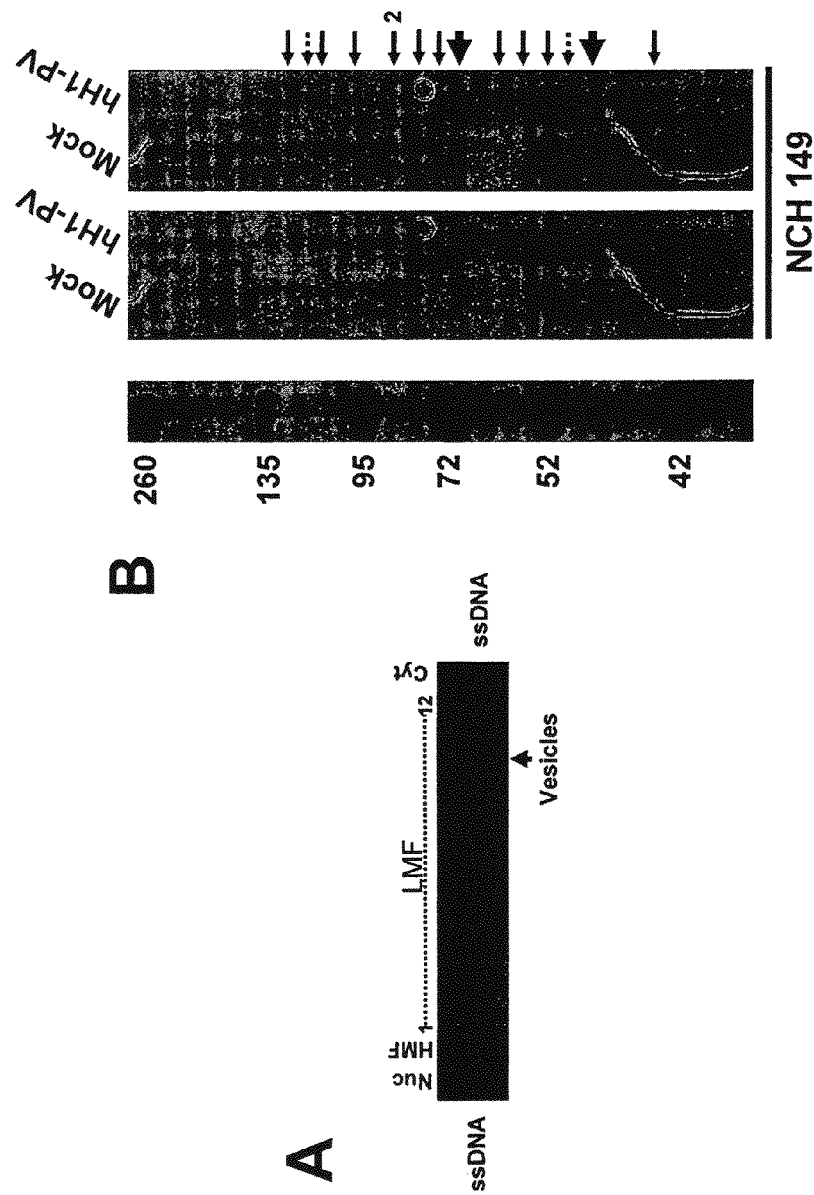

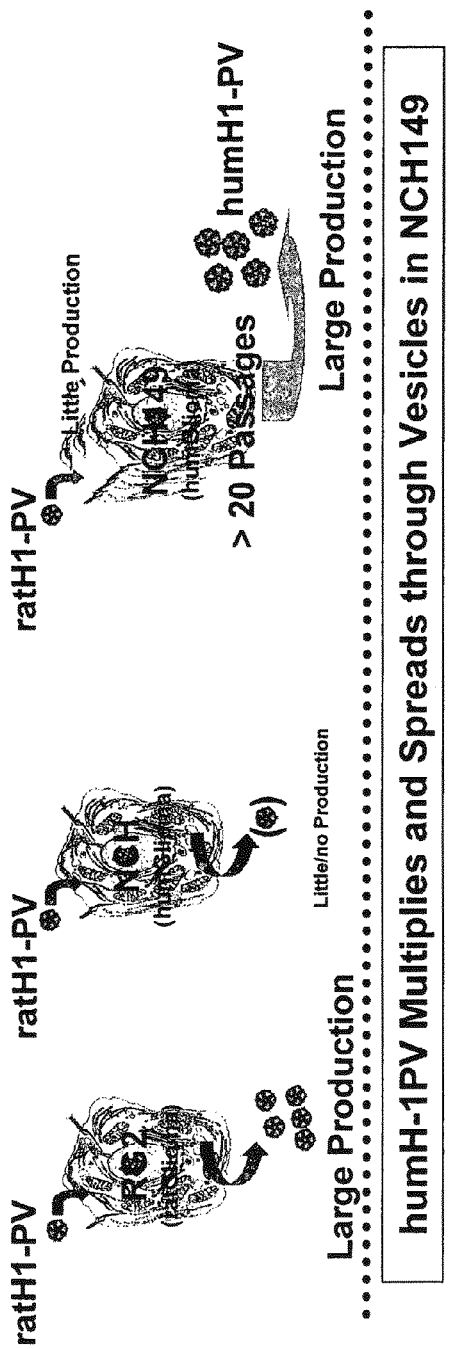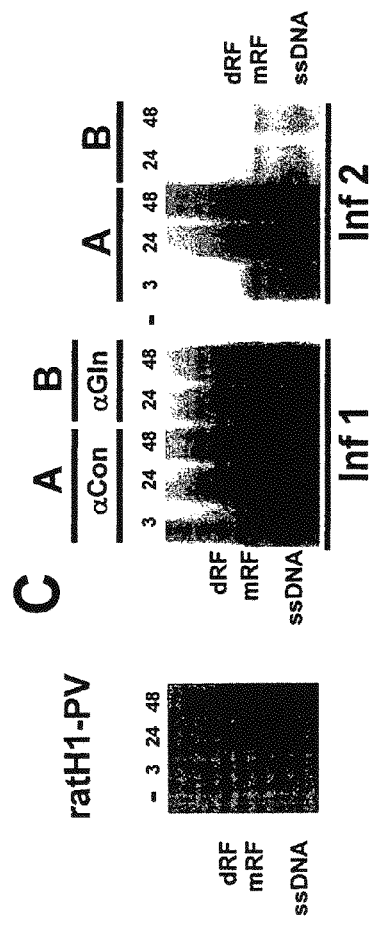
Fig. 1

Adaptation Leads to Changes of humH1-PV Non-structural Proteins in Human Glioma

A

| | 149 | ratH-1PV | humH-1PV | EC | |
|---|---|---|---|---|---|
| NS1 | | | | | Replication, Transcription, Cytotoxicity (signaling cascades, cytoskeleton) |
| NS2 | | | | | Replication, Capsid formation |
| NS3 | | | | | Nuclear/Cytoplasmic Transport |
| VP1 VP2 | | | | | |

− 2 5 10 24 48 72   2 5 10 24 48 72   2 5

B ratH-1 (RG-2)   ratH-1 (NCH149)   humH-1 (NCH149)

Phosphorylations driving vDNA amplification

Fig. 3

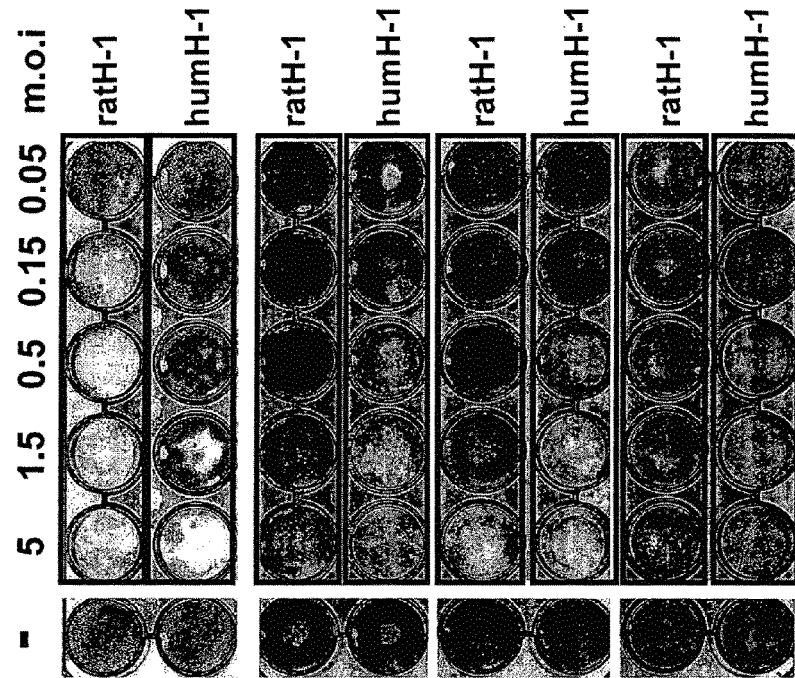
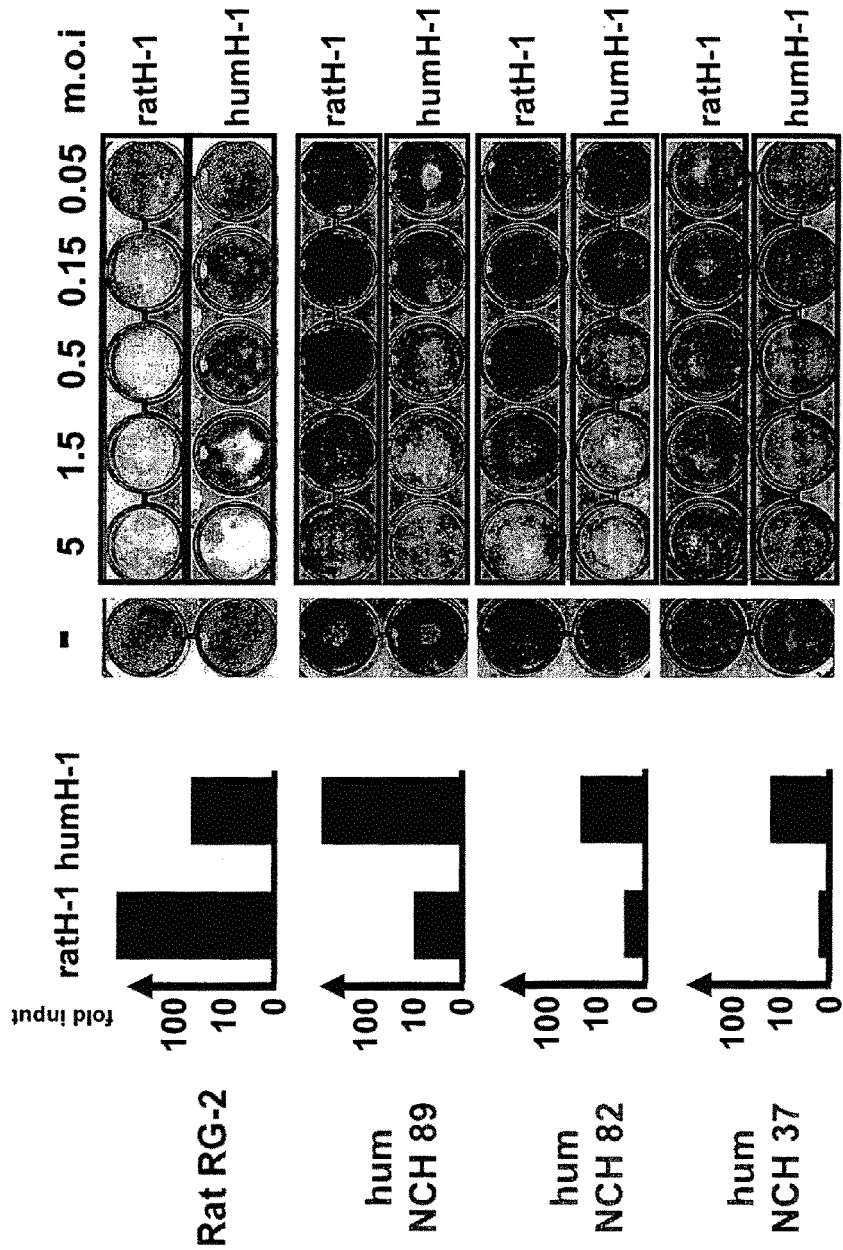
Fig. 4a
Fig. 4b

Fig. 6

Variation No 1: (deleted nts in italics)
2100-
GCACACCAAA TACTCCTGTT GCGGGCACTG
CAGCAAGCCA AAACACTGGG
GAGGCTGGTT CCACAGCCTG CCAAGGTGCT
CAACGGAGCC CAACCTGGTC
CGAGATCGAG -2211_SEQ ID NO: 1
Variation No 2: (changed nt in bold/italics)
3900-GCTGGCGGAGG ACTATGATGC -3921_ SEQ ID NO: 3
Variation No 3: (changed nt in bold/italics)
3950-ACAACACATGGC GAAAATTGGG -3971_SEQ ID NO: 4
Variation No 4: (changed nt in bold/italics)
4100-GCGAGAAAAAC GCCATAGCTG -4121_SEQ ID NO: 5
Variation No 5: (deleted nt °)
4660-TAT°AAAAAT AACATAATAT -4681_SEQ ID NO: 6
Variation No 6: (inserted nt in bold/italics)
4670-AACATAATAT GGTA*TT*GGTTAA-4691_SEQ ID NO 7
Variation No 7: (changed nt in bold/italics)
4690-CTGTAAAAAA CAATAGAACT -4711_SEQ ID NO: 8
Variation No 8: (inserted nt in italics)
4800-AGATAGA
ATATAAGAAGA*GATTTTGTATTTTAAAATAAATATAGTTAGTT*
GGTTAATGTTAGATAGA
ATA TAAAAAGATT -4821_SEQ ID NO: 9

Fig. 6b

Variation No 1b (Plaque #13): (deleted nts in italics)

2010-
CTCTGACTCC GAGAAGTACG CCTCTCAGCC AAAACTACGC
TCTTACTCCA CTTGCATCGG ACCTTGCGGA CCTAGCTCTA
GAGCCCTTGGA GCACACCAAA TACTCCTGTT GCGGGCACTG
CAGCAAGCCA AAACACTGGG GAGGCTGGTT *SEQ ID NO: 2
-2161

Protein Sequences H1-PV

NS1 SEQ ID NO: 10

```
MAGNAYSDEV LGVTNWLKDK SSQEVFSFVF KNENVQLNGK DIGNNSYRKE
LQDDELKSLQ RGAETTWDQS EDMEWESAVD DMTKQVFIP DSLVKKCLFE
VLSTKNIAPS NVTWFVQHEW GKDPGWHCHV LIGGKDFSQP QEHWRRQLM
VYWSRLVTA CWVQLTPAER IKLREIAKDS EWVTLITYEH RHTKKDYTKC
VLFGNMIAYY FLSKKKICTS PPRDGGYFLS SDSGWKTNFL KEGERHLVSK
LYTDEMKPEI VKTTVTTAQR AKRGRIQTRE RVSIKYTIKE IVHKRVTSPE
DWMMQPDSY IEMMAQPCGE NLLKNTLRIC TLTLARTKTA PDLILEKART
SKLANFSMAS TKTCRIFAEH GWNYIKVCHA ICCVLNRQGG KRNFVLPHGP
ASTGKSIIAQ AIAQAVGNVG CYNAANVNPP FNDCTNKNLI WVEEAGMPGQ
QVMQFKAICS GQTIRIDQRG KGSKQIEPTP VIMTTNENIT VVRIGCKERP
EHTQPIRDRM LNIHLTRTLP GDPGLVDKHE WPLICAWLVK NGYQSTMACY
CAKWGKVPDW SEDWAEPKLD TPINSLGSMR SPSLTDRSTP LSQMYALTPL
ASDLADLALE PWSTPNT... LESDFNKELT LD
    dl P124Q; EC180K
```

NS2 SEQ ID NO: 11

```
MAGNAYSDEV LGVTNWLKDK SSQEVFSFVF KNENVQLNGK DIGNNSYRKE
LQDDELKSLQ RGAETTWDQS EDMEWESAVD MTKKFNALTI SDSEKYASQP
KLRSYSTCIG PQGPSSRALE HTKYSCCGHC KLPSEHGG... 
NLVRDRGGFR SLLQSRFVGE KLQRGADLGL RYGVLMYDYL FYRPEITWF
D1: dl aa126-153
```

VP1/2 SEQ ID NO: 12

```
MAPPAKRAKR GWVPGTKYL GPCNSLDQCE PTNPSDAAAK EHDEAYDQYI
KSGKNPYLYF SPADQRFIDQ TKDARDWGGK VGHYFFRTKR AFAPKLSTDS
EPCTSGTSGV SRPGKRTKPP AHIFVNPARA KKKRASLAAQ QRTLT
NSDGTETNQP DTGIANARVE RSADGGGSSG GGGSGGGGI GVSTGTYDNQ
TTYKFLGDGW VEITAHASRL LHILGMPPSEN YCRVTVHNNQ TYGHGTKVKG
     N(lB)
NMAYDTHQQI WTPWSLVDAN AWGVWFQPSD WQFIQNSMRS LNLDSLSQEL
FNVVKTVTE QQGAGQDAIK VYNNDLTACM MVALDSNNIL PYTPAAQTSR
TLGFYPWKPT APAPYRYIFF MPRQLSVTSS NSARGTQITD TIGEPQALNS
                                           GMPPR(sb)
QPFTIENTLP ITTLRTGDEF TNGTVIFNTD PLKLTHTWQT NRHLACLQGI
TDLPTSDTAT ASLTANGDRF GSTQTQNVNY VTEALRTRPA QIGFMQFHDN
FRANRGGPFK VPVVPLDITA GRDWDAMGAI RPNYGKQHGE EWAKQGRAPE
RYTWDAIDSA AGRDTARCFV QSAPISIPPN CNQILQREDA IAGRTNMYT
NVFNSYGPLS APPHPDPIYP NGQIWDKELD LEHKPRLHVT APFVCKNNPP
    N(sb)
GQLFVHLGPN LTDQFDPNST TVSRLVTYST FYWKGILKFK AKLRPRLLTWN
PVYQATTDSV ANSYMNVKKW LPSATGNMHS DPLICRPVPH MTY
  26 E87A/3 D391M/4 D439E
```

Fig. 8

Protein Sequences H1-PV Plaque #13

NS1 SEQ ID NO: 14
MAGNAYSDEV LGVTNWLKDK SSQEVFSFVF KNENVQLNGK DIGWNSYRKE
LQDDELKSLQ RGAETTWDQS EDMEWESAVD DMTKKQVFIF DSLVKKCLFE
VLSTKNIAPS NVTWFVQHEW GKDPGWHCHV LIGGKDFSQP QGKWWRRQLN
VYWSRWLVTA CNVQLTPAER IKLREIAEDS EWVTLLTYKH KHTKKDYTKC
VLFGNMIAYY FLSKKKICTS PPRDGGYFLS SDSGWKTNFL KEGERHLVSK
LYTDEMKPET VETTVTTAQE AKRGRIQTRE EVSIKTTLKE LVHKRVTSPE
DWMMMQPDSY IEMMAQPGGE NLLKNTLEIC TLTLARTKTA FDLILEKAET
SKLANFSMAS TRTCRIFAEH GWNYIKVCHA ICCVLNRQGG KRNTVLFHGP
ASTGKSIIAQ AIAQAVGNVG CYNAANVNFP FNDCTNKNLI WVEEAGNFGQ
QVNQFKAICS GQTIRIDQKG KGSKQIEPTP VIMTTNENIT VVRIGCEERP
EHTQPIRDRM LNIHLTRTLP GDFGLVDKHE WPLICAWLVK NGYQSTMACY
CAKWGKVPDW SEDWAEPKLD TPINSLGSMR SPSLTPRSTP LSQNYALTPL
ASDLADLALE PWSTPNTPVA GTAASQNTGE AGSTACQGAQ RSPTWSEIEA
DLRACFSQEQ LESDFNEELT LD
D1b: dl aa587-628; P134Q; E380K

NS2 SEQ ID NO: 15
*MAGNAYSDEV LGVTNWLKDK SSQEVFSFVF KNENVQLNGK DIGWNSYRKE*
*LQDDELKSLQ RGAETTWDQS EDMEWESAVD MTKKFNALTI* SDSEKYASQP
KLRSYSTCLG PCGPSSRALE HTKYSCCGHC SKPKHNGGWF HSLPRCSTEP
NLVRDRGGFE SLLQSRTVGE RLQRGADLGL RYGVLMYDYL FYRPEITWF
D1b: dl aa95-135

VP[redacted]/2 SEQ ID NO: 16
*MAPPAKRAKR GWVPPGYKYL GPGNSLDQGE PTNPSDAAAK EHDEAYDQYI*
*KSGKNPYLYF SPADQRFIDQ TKDAKDWGGK VGHYFFRTKR AFAPKLSTDS*
*EPGTSGTSGV SRPGKRTKPP AHIFVNQARA KKKRASLAAQ QRTLT*
MSDGTETNQP DTGIANARVE RSADGGGSSG GGGGSGGGGI GVSTGTYDNQ
TTYKFLGDGW VEITAHASRL LHLGMPPSEN YCRVTVHNNQ TTGHGTKVKG
D(in)
NMAYDTHQQI WTPWSLVDAN AWGVWFQPSD WQFIQNSMES LNLDSLSQEL
FNVVVKTVTE QQGAGQDAIK VYNNDLTACM MVALDSNNIL PYTPAAQTSE
TLGFYPWKPT APAPYRYYFF MPRQLSVTSS NSAEGTQITD TIGEPQALNS
GMPPR(sb)
QFFTIENTLP ITLLRTGDEF TTGTYIFNTD PLKLTHTWQT NRHLACLQGI
TDLPTSDTAT ASLTANGDRF GSTQTQNVNY VTEALRTRPA QIGFMQPHDN
FEANRGGPFK VPVVPLDITA GEDHDANGAI RFNYGKQHGE DWAKQGAAPE
RYTWDAIDSA AGRDTARCFV QSAPISIPPN QNQILQREDA IAGRTNMHYT
NVFNSYGPLS AFPHPDPIYP NGQIWDKELD LEHKPRLHVT APFVCKNNPP
N (sb)
GQLFVHLGPN LTDQFDPNST TVSRIVTYST FYWKGILKFK AKLRPNLTWN
PVYQATTDSV ANSYMNVKKW LPSATGNMHS DPLICRPVPH MTY
2: H374Y; 3: D391N; 4: D439S

MODIFIED RODENT PARVOVIRUS CAPABLE OF PROPAGATING AND SPREADING THROUGH HUMAN GLIOMAS

CROSS-REFERENCE TO RELATED PATENT APPLICATIONS

This application is a U.S. National Phase Application under 35 U.S.C. §371 of International Patent Application No, PCT/EP2011/002306, filed May 9, 2011, and claims the priority of European Patent Application No. 10004897.4, filed May 7, 2010, all of which are incorporated by reference herein. The International Application was published in as International Publication No. WO 2011/138053 under PCT Article 21(2).

The present invention relates to a rodent parvovirus variant capable of propagating and spreading through human tumor cells which is obtainable by serially passaging a rodent parvovirus as starting strain in semi-permissive human tumor cells. It also relates to a parvovirus variant capable of propagating and spreading through human tumor cells characterized by particular amino acid deletions and/or substitutions, e.g. a deletion of several amino acids in the C-terminus of NS1/middle exon of NS2. The present invention also relates to a pharmaceutical composition containing such parvovirus as well as its use for the treatment of cancer, preferably a glioblastoma.

Oncolytic viruses such as rodent parvoviuses represent novel tools for cancer treatment. Besides specifically killing cancer cells (oncolysis), these agents also provide danger signals prompting the immune system to eliminate virus-infected tumours. As a consequence of oncolytic events, the innate and adaptive immune systems gain access to tumour antigens, which results in cross-priming and vaccination effects. Rodent parvoviruses are single-stranded DNA viruses possessing intrinsic oncolytic activity, i.e. they preferentially replicate in and kill cancer cells of both murine and human origin.

Glioblastoma is a devastating disease with only limited treatment possibilities. Evidently, the prognosis for patients requires new therapies. The replication competent oncolytic viruses discussed above are considered promising since they are able to spread through malignant tissues and induce anti-tumor immune-responses. Among them, rodent parvoviruses appear to be excellent candidates, due to their natural oncotropism, their capacity to infect human cells, the specific toxicity for neoplastic cells, and the low pathogenicity for humans. In a rat model, H1-PV was able to cause a complete regression of established gliomas without any relaps and they proved able to target various human gliomas, thereby efficiently killing these cells irrespective of their acquired resistance towards known death inducers. Although, H1-PV proved able to infect and efficiently kill most of the human glioblastoma cell lines tested so far, the majority of these cells resisted efficient virus replication, progeny particle production and spreading. This failure to propagate and spread through human tumor tissue could have major impact for the treatment efficacy of human gliomas in vivo, not only because cell killing is limited to a single hit event reaching only a limited proportion of the tumor cells, but also due to the lack of an active intracellular transport of progeny virions to the cell surface.

Therefore, it is the object of the present invention to overcame this draw back of the prior art strains, i.e., to provide parvoviruses that are capable to propagate and spread through human tumor tissue.

According to the invention this is achieved by the subject matters defined in the claims. Initial experiments of the inventors have shown that progeny PV virions are shuttled from the nucleus to the cell periphery through vesicles prior to cell lysis where they are released into the medium supernatant. Moreover, this vesicular egress is associated with multiple intracellular proteins (including potential tumor antigens) which are carried as "co-cargo" to the cell surface and might contribute to the host anti-tumor immune stimulation. To mend the defects of the original H1-PV isolate (pSR19) in virus propagation and spreading in human glioblastoma, the inventors aimed to obtain propagation competent H1-PV variants through serial passaging in semi-permissive patient-derived human glioblastoma cell lines, i.e., to circumvent potential bottle-necks during the infection process (uncoating, delivery of the viral genome to the nucleus, double-strand conversion), infectious clone DNA of H1-PV (pSR-19) was transfected into different human glioblastoma cell lines (e.g. NCH149, NCH82, NCH89) and this replication competent DNA was passaged until cytopathic effects became visible. Additional viral passages (>15) were made combining cell associated progeny virions obtained through repeated freezing and thawing in vTE pH 8.7 with medium released viruses through infection. A pool of propagation competent viruses was then analyzed after 25 passages on NCH149 cells presenting efficient viral DNA amplification, generation of progeny virions and spreading through a variety of human glioblastoma cultures. From this original pool, individual virus clones were isolated through plaque-purification on NB 324K cells, amplified again on NCH149 cells, cloned and sequenced.

The genetic analysis of all H1-PV variants has revealed a deletion of 84 nts affecting 28 amino acids of the coding region of NS1 (C-terminus) and NS2 and a single cytosine to thymidine transition at position 3913 changing His374 to Tyr in VP2. Two additional guanidine to adenosine substitutions in the VP2 region (3964 and 4108) leading to a change from Asp391 to Asn and Asp439 to Ser have only been assigned to two isolates. A few changes in the 3' non-coding regions remained of various prevalence. Apparently, the region approximately between nts 2000 to 2200 comprises a hot-spot of variability allowing H1-PV through modulation of NS1/NS2 function to adapt to the host environment. Therefore, it is possible to modify actively the host range of H1-PV, but also the other closely related rat PV strains, H3 and TVX through insertion/deletions within this region.

The newly generated H1-PV variants are able to propagate and spread through human glioblastoma cell(line)s. This allows an increased infection/destruction of already established human tumors and in consequence it is expected to give rise to a better anti-tumor immune stimulation. In agreement with the inventors' previous findings of parvovirus vesicular egress, it is reasonable to assume that the co-transport of intracellular proteins to the surface might serve to unmask tumor cells for a host immune response. This co-cargo effect is not present in absence of progeny virion formation using the original H1-PV isolate (pSR-19).

SUMMARY OF THE PRESENT INVENTION

With the adaptation process (passaging) in semi-permissive cells as outlined in the examples an H1-PV variant proficient for propagation in many other human glioblastoma cell lines could be generated. The outlined procedure can be expanded to other human tumor cell(line)s including tumor stem cells.

Adaptation of the rat H1-PV on human glioblastoma cells led to a deletion in the C-terminus of H1 NS1/middle exon of NS2. This region represents a hot spot area for variation determining H1-PV host range and with additional adapatations/analyses of other so far uncharacterized rodent PV isolates additional variations can be found in this area.

Besides generating an H1-PV variant that is potentially able to spread from cell to cell in human glioblastoma tumor tissue and therefore has a higher potential for tumor cell killing (as indicated by the fitness assays), progeny particles of this isolate are actively transported to the cell periphery through vesicles. Besides newly synthesized virions, multiple cellular proteins being associated with such vesicles were found after infection which were not present in non-infected human glioblastoma cells. This co-cargo could serve to unmask tumor cells to make them available for the host immune system, thereby contributing for a virus-induced anti-tumor immune response.

BRIEF DESCRIPTION OF THE DRAWINGS

FIG. 1:

(Top) Schematical Presentation of the Adaptation Approach

Rat parvovirus H1-PV readily propagates in transformed rat cells such as rat glioma RG-2 (left), but is limited to produce and spread in human glioblastoma cell lines. To overcome these limitations, serial passages were performed in semi-permissive human glioblastoma allowing mutations and amplification of permissive H1-PV variants to occur. Propagation competent variants were obtained/analyzed after 20 consecutive passages in NCH149 cells.

(B, C) Determination of Viral DNA Amplification in NCH149

NCH149 cells were infected with 10 pfu/cell H1-PV and the presence of replication intermediates was measured by Southern blotting after indicated times post infection.

(B) Infection with rat H1-PV (pSR19).

(C) Primary and secondary DNA amplification with human glioma adapted H1-PV, determination of gelsolin functioning for vesicular egress and spreading. Inf 1, primary infection, Inf 2, supernatants from Inf 1 were used to infect naive NCH149 cells. The generation of viral replication intermediates was measured by Southern blotting. αCon, control serum; αGln, neutralizing antiserum raised against gelsolin; dRF, dimeric replication intermediate; mRF, monomeric replication intermediate; ssDNA, progeny virus particles=single-stranded virus genomes.

FIG. 2: Determination of H1-PV vesicular egress and identification of "co-cargo"

(A) NCH149 cells were infected with 10 pfu/cell human glioma adapted H1-PV and fractionated for nuclei (Nuc), heavy mitochondrial fraction (HMF), and light mitochondrial fraction (LMF), containing cellular vesicles. To determine the presence of progeny virions in the vesicular fraction, LMF components were further separated by iodexanol gradients and the presence of virion DNA was measured by Southern blotting as compared to the presence of vesicular markers (determined by Western blotting).

(B) Determination of vesicular proteins in hgH1-PV and mock infected NCH149 cells. Vesicles were purified as described under (A) and analyzed for their protein content by SDS-PAGE and silver staining. Proteins overrepresented in hgH1-PV infected cellular vesicles are indicated by arrows.

FIG. 3:

(A) Determination of Viral Protein Expression After Infection of NCH149 Cells with Rat (pSR19) Versus Human Glioma Adapted H1-PV NCH149 cells were infected with 10 pfu/cell and harvested at indicated times post infection. Accumulation of viral proteins were determined by Western blotting. Encircles (red) the large heterogeneity of NS1 produced after hgH1-PV infection and the larger accumulation of NS2 and NS3 (blue).

(B) RG-2 and NCH149 Cells were Infected with the Indicated Virus Preparations at a Multiplicity of 10, and Metabolically Labelled with $^{32}$P-Orthophosphate at 24 h p.i. for Four Hours Cells were harvested, NS1 purified by immunoprecipitations and SDS-PAGE and the tryptic phosphopeptide pattern was determined by two-dimensional electrophoresis/chromatography. The phosphopeptide pattern of NS1 produced by rat H1-PV (pSR-19) in rat glioma (left), NCH149 (middle), as well as hgH1-PV in NCH149 cells (right) are shown. Encircled: phosphorylations known to drive viral DNA amplification.

FIG. 4:

(A) Multiplication of Input Virus After Infection of Various Target Cell Lines

Indicated cell lines were infected at a multiplicity 10, washed and harvested 4 (Input virus) 24 and 48 h post infection. Cell and medium associated virus was determined by plaque assay. The average amplification 24 and 48 h post infection is expressed over input (4 h) virus titer.

(B) Virus Fitness Assay

Target cell lines were seeded in 24 well dishes, infected at indicated multiplicities with the appropriate virus preparations, and living cells were fixed and stained with crystal violet 6 days post infection.

FIG. 5:

Top: Genome organization of H1-PV with indication of variation found after adaptation in human glioma Middle section: PCR-fragments generated from plaque purified virus preparations Bottom: Genetic determination of plaque purified hgH1-PV variants Cloned PCR fragments are indicated by black lines, sequenced material is indicated by dotted squares and the presence of the individual variations are indicated in green.

FIG. **5*b***: H1-PV variant plaque #13:

After the initial characterization of five plaques (1,2,3,5, and 8) an additional plaque derived from the same adaptation experiment was cloned and sequenced (plaque #13). This additional variant was recognized by a different deletion in the C-terminal part of NS1/middle exon of NS2 together with mutations 2 and 6 previously found in the first round of characterizations (plaques 1 through 8).

FIG. 6: Detailed characterization of all genetic variations found by sequencing of individual plaques FIG. **6*b***: Detailed characterization of the additional deletion in the coding region of NS1/NS2 found by sequencing of plaque #13.

FIG. 7: Virus fitness assay of virus stocks derived from individual plaque isolates FIG. 8: Changes in the H1-PV Protein sequences as deduced from the nucleotide changes obtained by DNA-sequencing and summarized in FIG. 6.

Protein sequences corresponding to the H1-PV nucleotide sequence published under NC_001358. The three exons of NS2p as deduced from the transcription pattern of Qiu et al., (2006) are indicated in italics (common Nterminus with NS1=exon1)–regular (middle exon)–italics(C-terminal exon

[unique for each NS2 isoform). Amended sequencing errors are indicated in light gray (these differences to the published sequence were found in all our isolates as well). Variations created through passaging in NCH149 cells are indicated in bold and marked with light-grey. VP1-specific sequences are denoted in italics.

FIG. 8*b*: Changes in the H1-PV protein sequences in plaque #13 as deduced from nucleotide changes obtained by DNA-sequencing and summarized in FIG. 6*b*.

Protein sequences corresponding to the H1-PV nucleotide sequence published under NC 001358. The three exons of NS2p as deduced from the transcription pattern of Qiu et al., (2006) are indicated in italics (common Nterminus with NS1=exon1)–regular (middle exon)–italics(C-terminal exon [unique for each NS2 isoform).Amended sequencing errors are indicated in light gray (these differences to the published sequence were found in all our isolates as well). Variations created through passaging in NCH149 cells are indicated in bold. VP1-specific sequences are denoted in italics. Coding changes of the deletion D1b and VP1/2 mut4 of Plaque #13 are given in bold and marked with light-gray.

FIG. 9: Impact of H1-PV infection (wildtype and plaque #3), respectively on tumor growth of U87 glioblastoma cells subcutaneously implanted into nude balb/c mice.

DETAILED DESCRIPTION OF THE PRESENT INVENTION

The present invention provides in a first aspect a parvovirus variant capable of propagating and spreading through human tumor cells which is obtainable by serially passaging a rodent parvovirus as starting strain in semi-permissive human tumor cells.

In addition, the present invention provides in a second aspect a parvovirus variant capable of propagating and spreading through human tumor cells characterized in that it comprises a deletion of 28 amino acids from position 619 to 646 (Rhode and Paradiso, 1983) in the C-terminus of NS1/position 126 to 153 in the middle exon of NS2 (Rhode and Paradiso, 1983; Qiu et al., 2006).

The present invention also provides a parvovirus variant capable of propagating and spreading through human tumor cells characterized in that it comprises the following amino acid substitution(s) in VP1/2:

(a) H374Y;

(b) D391N; and/or (c) D439S.

The term "propagating" as used herein means that the progeny virions of the parvovirus variant show amplification significantly over input levels (i.e. >5 fold).

The term "spreading through" as used herein means that the progeny virions of the parvovirus variant are capable not only of killing primarily infected cell populations, but are able to cause secondary infections of naive cells with particles produced during the first round of infection.

The term "semi-permissive" as used herein for characterizing the host cells means that the infection with the virus results in incomplete viral replication within the particular type of host cells but are characterized by viral DNA amplification and eventually low yields of progeny virions. The latter do not necessarily have to be infectious in the beginning of the procedure.

The expression "parvovirus" comprises any parvovirus, particularly a rodent parvovirus, such as minute virus of mice (MVM) and H-1 virus as well as related viruses or vectors based on such viruses or derivatives. The person skilled in the art can arrive at the parvovirus variant according to the present invention by subjecting a starting strain to serial passaging as outlined in the Examples, below, or by introducing a deletion resulting in the desired modification of the biological properties, i.e., capability of the parvovirus variant to propagate and spread through, thereby killing, human tumor cells starting from the known nucleic acid sequence and amino acid sequences of the non-structural proteins of parvoviruses, e.g., from parvovirus H-1 (Rhode and Paradiso, 1983; Qiu et al., 2006). The person skilled in the art can also easily assay whether a particular variant exhibits the desired biological properties recited by using the assays explained in the examples, below.

Preferably, the parvovirus variant of the invention is derived from parvovirus H-1 (H-1PV) or a related rodent parvovirus. Examples of preferred related rodent parvovirus are LuIII, Mouse minute virus (MMV), Mouse parvovirus (MPV), Rat minute virus (RMV), Rat parvovirus (RPV) or Rat virus (RV).

In principle, any tumor can be cured using a parvovirus variant of the present invention with gliomas being preferred.

A particular preferred glioma is a glioblastoma.

A preferred human semi-permissive tumor cell line is NCH149.

As regards the procedure of serial passaging, the person skilled in the art can easily determine how many passages are sufficient for arriving at a parvovirus of the present invention. In general, however, this method of the invention comprises at least 10 passages, preferably at least 20 to 25 passages, or more. Preferably, passaging is on NCH149 cells.

In order to ensure the purity and stability of the virus variants the individuals clones can be plaque-purified after passaging, preferably on NB 324K cells.

The present invention also provides a method of generating a parvovirus variant capable of propagating and spreading through human tumor cells said method comprising serially passaging a rodent parvovirus as starting strain in semi-permissive human tumor cells as described above and in the examples, below.

A further subject matter of the present invention relates to a nucleic acid, particularly a DNA, which codes for an above parvovirus variant.

A DNA according to the invention can be present in a vector and expression vector, respectively. A person skilled in the art is familiar with examples thereof. In the case of an expression vector for *E. coli* these are e.g. pGEMEX, pUC derivatives, pGEX-2T, pET3b, T7 based expression vectors and pQE-8. For the expression in yeast, e.g. pY100 and Ycpad1 have to be mentioned while e.g. pKCR, pEFBOS, cDM8, pMSCND, and pCEV4 have to be indicated for the expression in animal cells. The baculovirus expression vector pAcSGHisNT-A is especially suitable for the expression in insect cells.

In a preferred embodiment, the vector containing the DNA according to the invention is a virus, e.g. an adenovirus, vaccinia virus, an AAV virus or a parvovirus, such as MVM or H-1, a parvovirus being preferred. The vector may also be a retrovirus, such as MoMULV, MoMuLV, HaMuSV, MuMTV, RSV or GaLV.

For constructing expression vectors which contain the DNA according to the invention, it is possible to use general methods known in the art. These methods include e.g. in vitro recombination techniques, synthetic methods and in vivo recombination methods.

Furthermore, the present invention relates to host cells which contain the above described variants or vectors. These host cells include human 293(T), NBK, rat RG2 cells, NCH149, NCH82, or U87 cells. Methods of transforming these host cells, of phenotypically selecting transformants and of expressing the DNA according to the invention by using the above described vectors are known in the art.

Thus, the present invention also provides a method of producing the parvovirus variant of the invention, comprising the culturing of a host cell of the invention under suitable conditions and harvesting the parvovirus variant from the cells or the medium.

Moreover, the present invention relates to antibodies which specifically recognize an above describe parvovirus variant, i.e. the polypeptide region of the parvovirus variant where the deletion is located characterizing the rodent parvovirus variant in that it is capable of propagating and spreading through human gliomas. The antibodies can be monoclonal, polyclonal or synthetic antibodies or fragments thereof, e.g. Fab, Fv or scFV fragments. Preferably monoclonal antibodies are concerned. For the production it is favorable to immunize animals—particularly rabbits or chickens for a polyclonal antibody and mice for a monoclonal antibody—with an above parvovirus variant or with fragments thereof. Further boosters of the animals can be affected with the same parvovirus variant or with fragments thereof. The polyclonal antibody can then be obtained from the animal serum and egg yolk, respectively. The monoclonal antibody can be obtained according to standard methods, reference being made particularly to the method by Köhler and Milstein (Nature 256 (1975), 495) and Galfre (Meth. Enzymol. 73 (1981), 3). In this case, mouse myeloma cells are fused with spleen cells originating from the immunized animals. Antibodies according to the invention can be used in many ways, e.g. for the immunoprecipitation of the above described parvovirus variants or for the isolation thereof. The antibodies can be bound in immunoassays in liquid phase or to a solid carrier. In this connection, the antibodies can be labeled in various ways. The person skilled in the art is familiar with suitable markers and labeling methods. Examples of immunoassays are ELISA and RIA.

A kit is also provided for the application of the present invention. This kit comprises the following:

(a) a parvovirus variant according to the invention;
(b) a DNA according to the invention, e.g. an expression vector, particularly a parvovirus;
(c) an antibody according to the invention; and/or, optionally,
(d) conventional auxiliary agents, such as solvents, buffers, carriers, markers and controls.

Of component (a) to (d) one or more representatives can be present each.

The present invention also provides a pharmaceutical composition containing a parvovirus variant of the invention, vector or a cell producing said parvovirus variant ("parvotherapeutic agent" or "parvotherapeutic composition"), e.g. human 293(T), NBK or rat RG2 cells.

For administration, the parvotherapeutic agent can be combined with suitable pharmaceutical carriers. Suitable pharmaceutical carriers of a type well known in the art and readily commercially available, include phosphate buffered saline (PBS) solutions, water, emulsions such as oil/water emulsions, wetting agents of various types, sterile solutions, etc. Such carriers can be formulated with the parvotherapeutic agent(s) by conventional formulating methods for administration to the subject at a suitable dose.

Additional pharmaceutically compatible carriers can include gels, biosorbable matrix materials, implantation elements containing the therapeutic agent, or any other suitable vehicle, delivery or dispensing means or material(s).

Administration of the parvotherapeutic pharmaceutical compositions to a patient, e.g. a brain tumor patient, may be effected in any of numerous suitable ways, e.g., by intravenous, intraperetoneal, subcutaneous, intramuscular, topical, intradermal, intracranial, and intratumoral administration. The route of administration, of course, depends on the nature of the disease and the specific therapeutic agent(s) contained in the pharmaceutical composition.

If such parvotherapeutic agent(s) comprise infectious virus particles with the ability to penetrate through the blood-brain barrier, treatment can be performed or at least initiated by intravenous injection of the viral therapeutic agent, e.g., a H1-PV variant.

Since long-term intravenous treatment is susceptible to becoming inefficient as a result of the formation of neutralizing antibodies to the viral therapeutic agent, different modes of administration can be adopted after an initial regimen of intravenous viral administration, or such different administration techniques, e.g., intracranial or intratumoral virus administration, can be alternatively used throughout the entire course of parvoviral treatment.

As another specific administration technique, the parvotherapeutic agent (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus variant or derived vectors can also be injected, e.g., into a tumor, by stereotactic surgical techniques or by neuronavigation targeting techniques.

Administration of the parvoviral agents or compositions can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvotherapeutic composition is from an implanted device constructed and arranged to dispense the parvotherapeutic agent to the desired locus, e.g., tumor. For example, wafers can be employed that have been impregnated with the parvotherapeutic composition, e.g., a parvovirus H-1 variant, wherein the wafer is attached to the edges of the resection cavity at the conclusion of surgical tumor removal. Multiple wafers can be employed in such therapeutic intervention.

Cells that actively produce the parvotherapeutic agent, e.g., a parvovirus H-1 variant, or H-1 variant vectors, can be injected into the desired tumor, or into a tumoral cavity after tumor removal.

Combinations of two or more of the above-described administration modes can be employed in any suitable manner, e.g., concurrently, contemporaneously, or sequentially.

The dosage regimen of the parvotherapeutic agent is readily determinable within the skill of the art, by the attending physician based on patient data, observations and other clinical factors, including for example the patient's size, body surface area, age, sex, the particular virus, vector, cell, etc. to be administered, the time and route of administration, the tumor type and characteristics, general health of the patient, and other drugs or therapies to which the patient is being subjected.

Accordingly, the present invention also relates to the use of a parvovirus variant according to the present invention, a cell producing said parvovirus variant, a DNA, an expression vector or antibody of the present invention for the preparation of a pharmaceutical composition for the treatment of cancer. Brain tumors (preferably a glioma, medulloblastoma, meningioma or glioblastoma) are expected to be particularly amenable to treatment with an agent of the present invention.

The below examples explain the invention in more detail.

EXAMPLE 1

Adaptation of Rat H1-PV (pSR19) to Human Glioma

Infection of many human glioblastoma cell lines with H1-PV derived from pSR19 isolate (Accession No: NC_001358) led to the expression of viral proteins and in consequence cell killing irrespective of their resistance towards drug-induced apoptosis. However, monitoring viral DNA amplification and progeny particle production, with exception of NCH89, the majority of the tested human glioblastoma cell lines only allowed little DNA amplification and virtually no increase in progeny production (Herrero y Calle et al., 2004; DiPiazza et al., 2007). To mend this defect, it was aimed to obtain (a) propagation competent H1-PV variant(s) through serial passaging of pSR19 in human glioblastoma cells, which were competent for DNA amplification although the infectious progeny virion production was hampered. The infectious clone DNA of H1-PV, pSR19 was transfected into NCH149 cells, a cell line that was shown to allow low levels of DNA amplification by Southern blotting (FIG. 1B). Parvoviruses are dependent on (rapidly) growing cells, since conversion of the single-stranded genome to a double-stranded transcription template requires S-phase. Therefore, the initial inoculum (tranfected cells) was first amplified by dilutions of 1:4 after confluency on the surface. After reaching $4 \times 10^8$ cells, ¾ of the cells were harvested, progeny virions were released by repeated freezing and thawing into the supernatant, and a combination of naive and transfected cells was re-infected with these virions until confluency or CPE was obtained. This procedure was continued until passage 20-25.

EXAMPLE 2

Analyses of Human Glioma Adapted H1-PV

After more than 20 consecutive passages the inventors obtained a virus stock competent for viral DNA amplification, progeny virion production and spreading in NCH149 cultures. The properties of this virus pool were analyzed. As shown in FIG. 1C by Southern blotting, this virus pool was characterized by strong DNA amplification after infection of NCH149 cells, producing monomeric and dimeric replication intermediates as well as single-stranded virion DNA. Besides reflecting the production of genomic viral DNA, this latter form indicates the formation of progeny virions, since the generation of single-stranded DNA is associated with the packaging process. Moreover, when supernatants of infected cells were collected (Inf 1) to infect naive NCH149 cells (Inf 2) similar DNA amplification and generation of single-stranded virion DNA was observed, demonstrating production and release of large numbers of infectious progeny virions in NCH149 cells. Indeed, release of progeny virions into the medium supernatants is dependent on the activity of cellular gelsolin, since application of neutralizing gelsolin antibodies inhibited this process. This dependency on gelsolin for the release of progeny virions indicates the involvement of an active vesicular transport to the cell periphery of progeny virions (Bar et al., 2008).

As shown in FIG. 2A by Southern blotting of the single-stranded progeny virion DNA after biochemical fractionations progeny H1-PV variant particles are found being strongly associated with vesicular fractions of infected cells. Moreover, by comparing vesicles from non-infected versus infected NCH149 cells analyzing the protein content by silver-staining a number of proteins being associated with virion-containing vesicular fractions, while being absent in non-infected cells was identified. The nature of these proteins is currently determined by MS/MS analyses.

Then, the nature of the virus modification(s) causing the permissive phenotype in NCH149 cells was identified. Original H1-PV (pSR19) was produced in rat RG-2 glioma, whereas the adapted H1-PV variant (hgH1-PV) was generated in NCH149. Both virus stocks were titrated by plaque assays in permissive NB324K cells. Infections were performed at a multiplicity of 10 in NCH149 cells and the production of viral proteins was determined in a time-course experiment by Western blotting. As shown in FIG. 3A, remarkable differences in the expression levels of the small non-structural proteins NS2 and NS3 were observed, while NS1 from hgH1-PV proved to be by far more heterogenous than NS1 from pSR19. NS1 is a multifunctional phosphoprotein, which is required for many processes during virus amplifications and is regulated for its functioning by differential phosphorylations. Indeed, as shown in FIG. 3B, when the phosphorylation patterns of NS1 obtained from pSR19 after infections of rat RG-2 cells and human NCH149 cells was analyzed the lack of two characteristic peptides after infection of NCH149 (encircled) was observed. In contrast, hgH1-PV was able to generate these phosphopeptides (and an additional peptide marked with an arrow), accounting for the differences in the migration pattern observed by Western blotting. Moreover, detailed functional analyses of the MVM NS1 phosphorylation (pattern), which closely resembles the one observed for pSR19 in RG-2/hgH1-PV in NCH149 suggests that the two encircled peptides are important phosphorylations involved in the replicative functions of the NS1 protein.

Finally, the adapted hgH1-PV stock was tested for its fitness to propagate and spread through a variety of (human) glioblastoma cultures in comparison to the pSR19 isolate. As shown in FIG. 4. in addition to NCH149 cells, all other human glioblastoma cell lines tested so far proved to be proficient to amplify hgH1-PV (but not pSR19) progeny virions at least ten fold above input levels and proved superior to pSR19 to spread through the cultures.

EXAMPLE 3

Genetic Characterization of Human Glioma Adapted H1-PV

Figure 5:
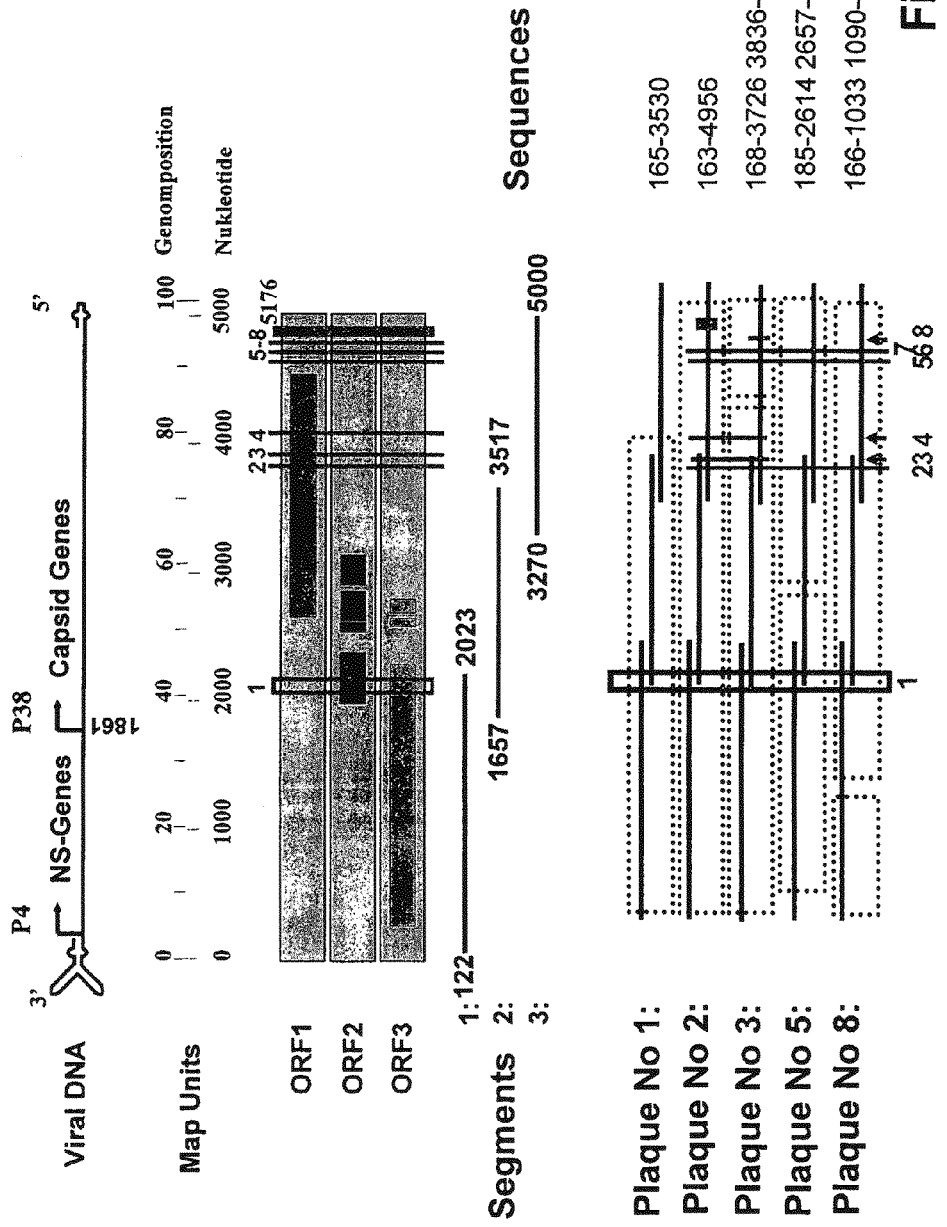
Figure 5B:
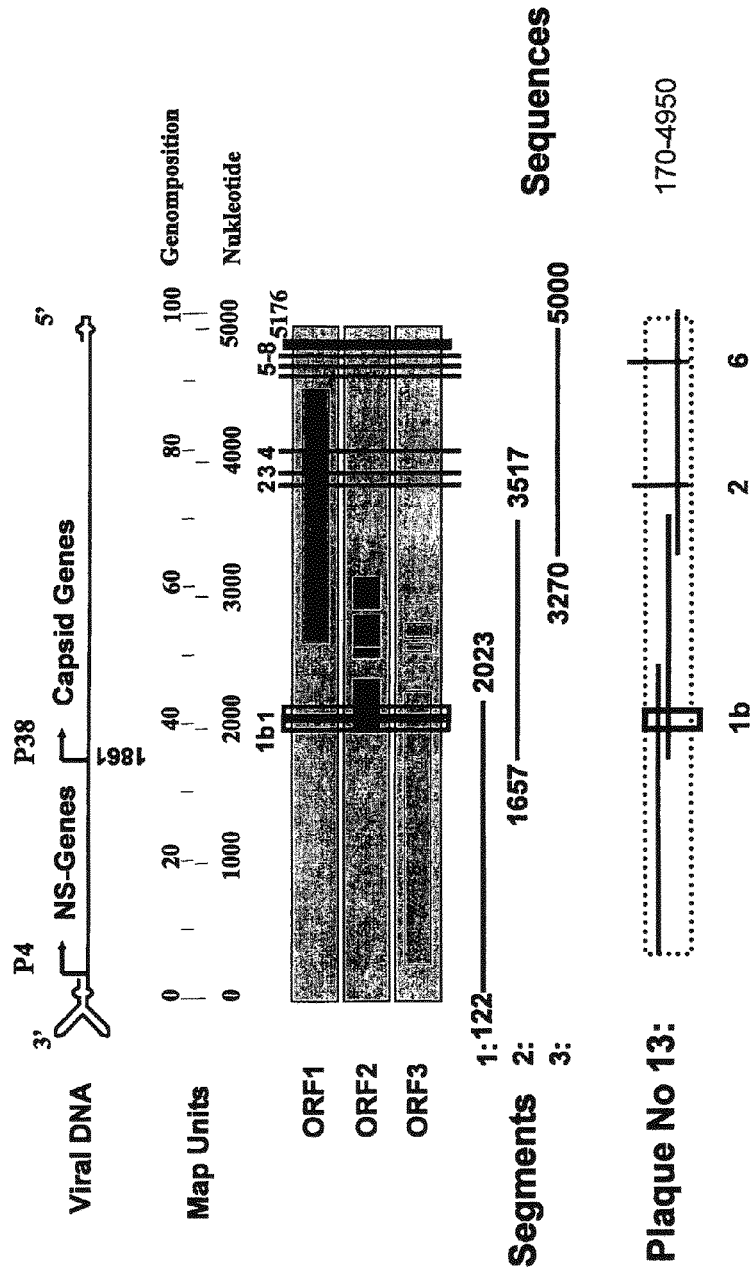

To determine genetic variations hgH1-PV acquired during passaging in NCH149 as compared to the original inoculum (pSR19), endpoint titrations were performed to plaque purify individual virus variants and virion DNA was isolated. As shown in FIGS. 5 and 5b, DNA of six individual plaques was obtained, the whole coding region was amplified by PCR in three steps and the overlapping fragments were cloned into pCR2.1. Genetic variations were determined by sequencing and compared to the published sequence of pSR19 (Accession No NC_001358). Mutations as compared to the pSR19 sequence found to be present on the individual plaque isolates are indicated, numbered and positioned in the H1-map. The detailed sequence alterations are shown in FIGS. 6 and 6b.

Figure 7:
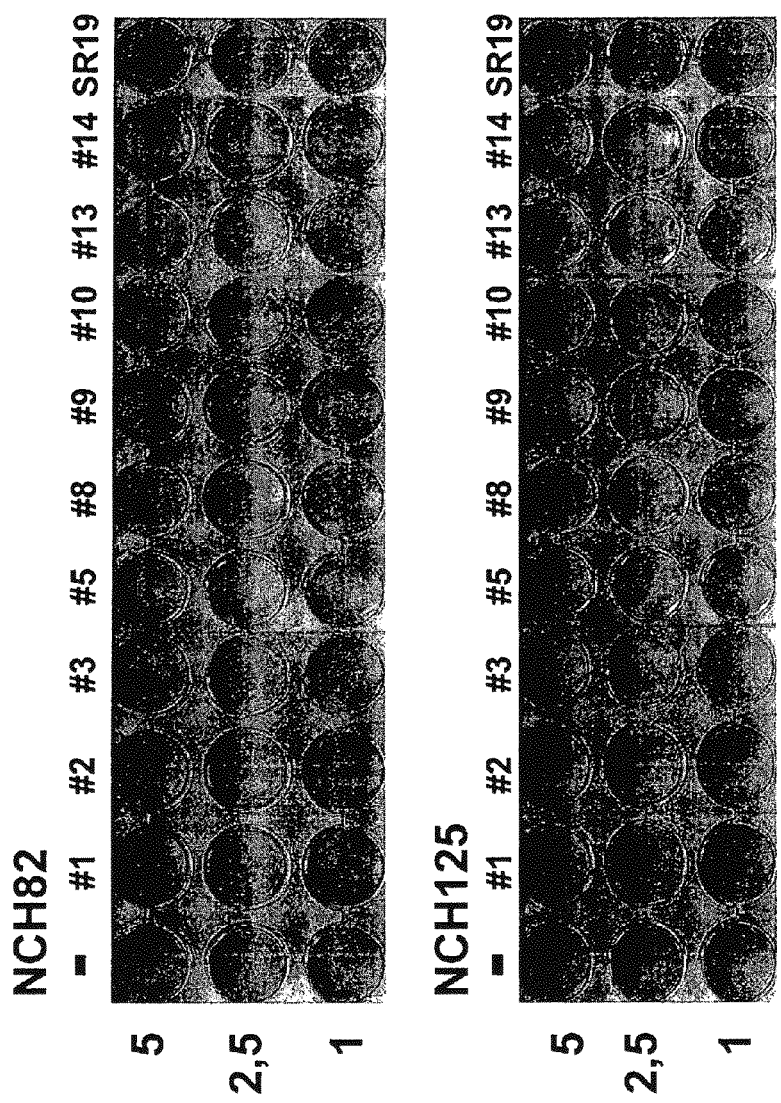
Figure 9:
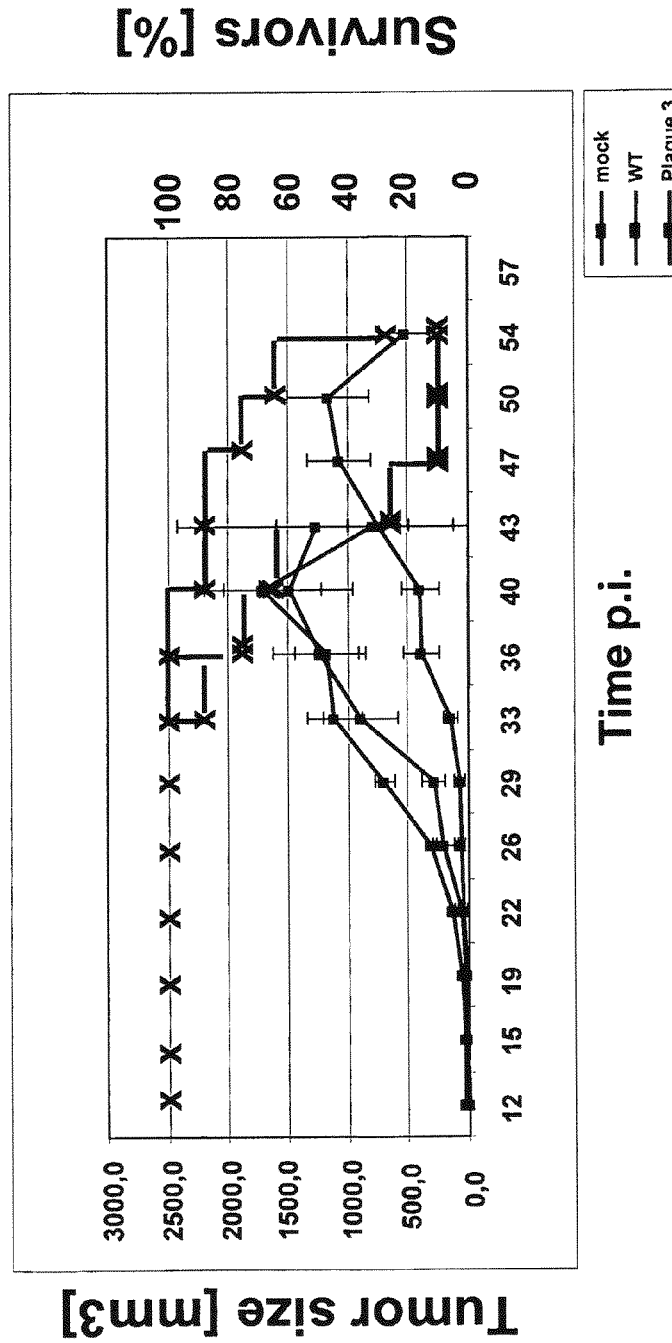
Figure 9A:
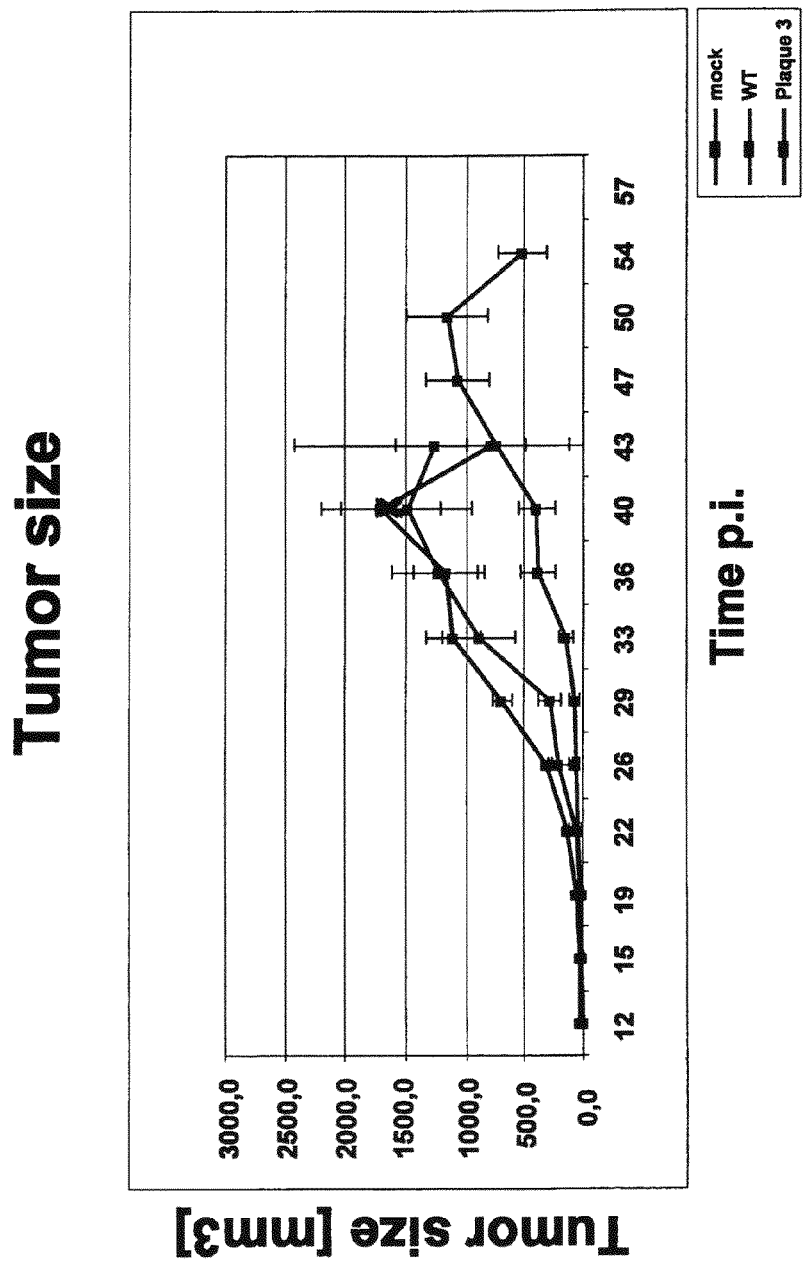
Figure 9B:
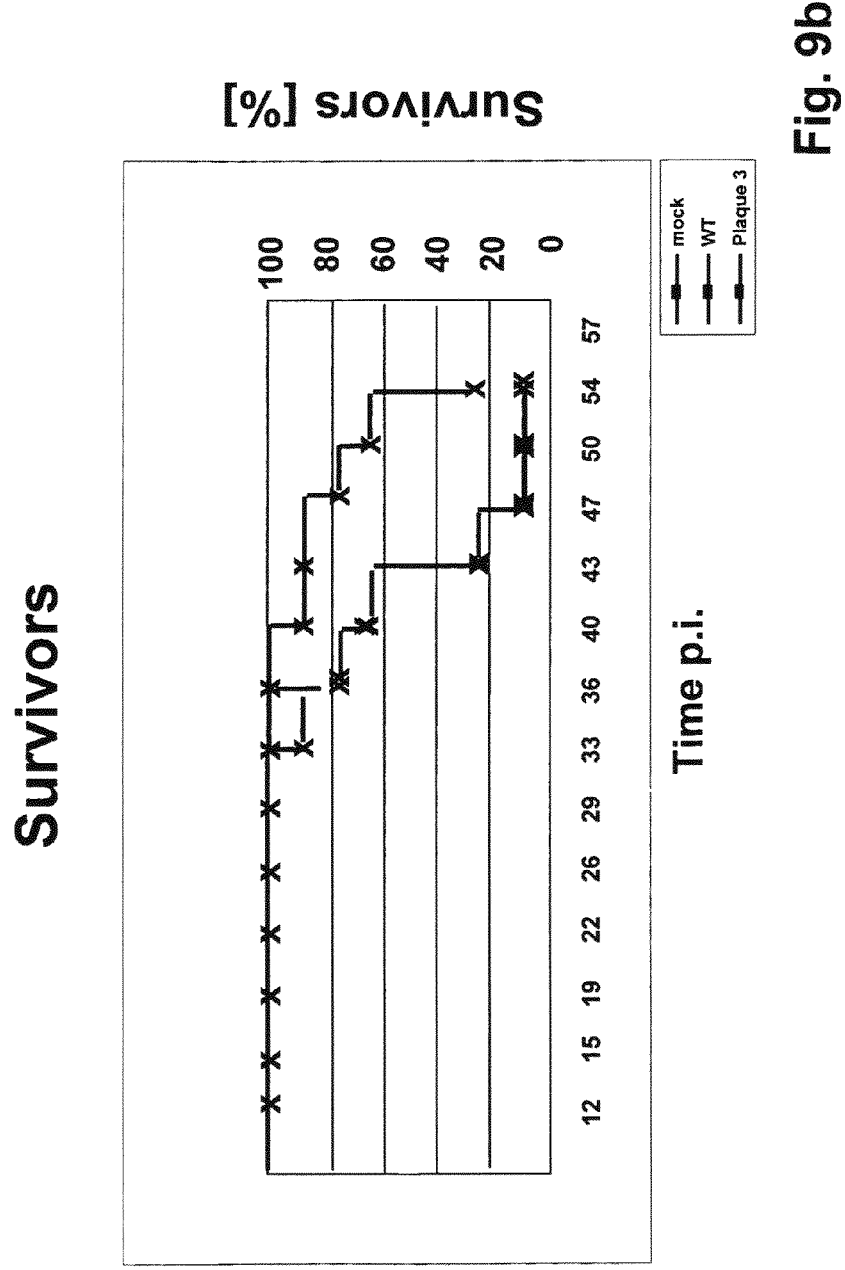

To further characterize the properties of individual clones, virus stock of individual plaque isolates was generated and their fitness to spread and kill human glioblastoma cell cultures in comparison to pSR19 generated in rat RG-2 cells was tested. As shown in FIG. 7, all isolates harbouring a deletion mutant in the C-terminal part of NS1/middle exon of NS2 surpassed pSR19 in their fitness to spread and kill human glioblastoma cells, confirming the initial findings with the pooled variants and demonstrating that the deletion mutant is responsible for the observed host range switch.

EXAMPLE 4

Impact of H1-PV Infection (Wildtype and Plague #3) on Tumor Growth

U87 glioblastoma cells were infected or not ex vivo with a MOI of 1.5 pfu/cell. (WT:H-1PV wildtype; Plaque #3: adapted H-1PV derived from plaque #3, mock: uninfected U87 cells). Cells were washed and dissolved in PBS 4 h p.i. and $2\times10^6$ mock or H-1PV infected cells in 100 μl PBS were implanted subcutaneously into 8 mice per group. Tumour size (length, width, height) was measured mechanically with a calliper twice a week, starting 12 days after tumour cell implantation. Volume was calculated as follows: $\frac{1}{2}\times length\times width^2$. Animals were sacrificed at a tumour size of maximum 2500 $mm^3$, in case of appearance of peritoneal carcinosis or malignant ascites. All surviving animals were sacrificed at day 61 after cell implantation. (1×WT, 2×Plaque #3) as indicated by “survivors”. It was shown in FIGS. 9, 9*a* and 9*b* that the tumor inhibition of plaque #3 was stronger than with H-1PV wild type. Furthermore, plaque #3 led to more survivors than H-1PV wild type.

LIST OF REFERENCES

Rhode, S. L. III and Paradiso, P. R. (1983. Parvovirus genome: nucleotide sequence of H-1 and mapping of its genes by hybrid-arrested translation. J. Virol. 45, 173-184.

Qiu, J., Yoto, Y., Tullis, G., and Pintel, D. J. (2006). Parvovirus processing strategies. pp. 253-274. In “Parvoviruses” Eds. Kerr, J. R., Cotmore, S. F., Bloom, M. E., Linden, R. M., and Parrish, C. R. Hodder Arnold, London.

The invention claimed is:

1. A genetically modified parvovirus comprising a deletion consisting of 28 amino acids from position 619 to 646 in the C-terminus of NS1 and from position 126 to 153 of NS2 of parvovirus strain H1-PV, or the corresponding positions of NS1 and NS2 in another parvovirus strain, wherein the virus propagates and spreads through human tumor cells.

2. The parvovirus of claim 1, further comprising one or more of the following amino acid substitution(s) in VP1/2:
   (a) H374Y;
   (b) D391N; and
   (c) D439S.

3. The parvovirus of claim 1, capable of propagating and spreading through human tumor cells by serially passaging a rodent parovirus as a starting strain in semi-permissive human tumor cells.

4. The parvovirus of claim 1, wherein the starting strain is a rat parvovirus.

5. The parvovirus of claim 4, wherein the rat parvovirus is H1-PV.

6. The parvovirus of claim 1, wherein the tumor cells are glioma cells.

7. The parvovirus of claim 6, wherein the glioma is a glioblastoma.

8. The variant of claim 3, wherein the semipermissive human tumor cells are NCH149 cells.

9. The parvovirus of claim 3, wherein the serial passaging comprises at least 10 passages.

10. The parvovirus according to claim 3, wherein after the rodent parvovirus undergo passaging to form individual virus clones, the individual virus clones are plaque-purified.

11. The parvovirus of claim 10, wherein the virus clones are plaque-purified on NB 324K cells.

12. An expression vector, comprising a DNA molecule encoding the parvovirus according to claim 1.

13. A host cell containing the parvovirus of claim 1.

14. A kit comprising:
   the parvovirus of claim 1; and
   optionally further comprises one or more auxiliary agents, wherein the auxiliary agents are solvents, buffers, carriers, markers and controls.

15. A pharmaceutical composition containing a parvovirus according to claim 1.

16. The parvovirus of claim 1, further comprising one or more amino acid substitution(s) in VP1/2.

17. The parvovirus of claim 2, capable of propagating and spreading through human tumor cells by serially passaging a rodent parvovirus as starting strain in semi- permissive human tumor cells.

18. The parvovirus of claim 2, wherein the starting strain is a rat parvovirus.

19. The parvovirus of claim 18, wherein the rat parvovirus is H1-PV.

20. The parvovirus of claim 2, wherein the tumor cells are glioma cells.

21. The parvovorius of claim 20, wherein the glioma is a glioblastoma.

22. The parvovirus of claim 17, wherein the semipermissive human tumor cells are NCH149 cells.

23. The parvovirus of claim 17, wherein the serial passaging comprises at least 10 passages.

24. The parvovirus according to claim 17, wherein after the rodent parvovirus undergo passaging to form individual virus clones, the individual virus clones are plaque-purified.

25. The parvovirus of claim 24, wherein the virus clones are plaque-purified on NB 324K cells.

26. An expression vector, comprising a DNA molecule encoding the parvovirus according to claim 2.

27. A host cell containing the parvovirus of claim 2.

28. A kit comprising the parvovirus of claim 2, and optionally further comprises one or more auxiliary agents, wherein the auxiliary agents are solvents, buffers, carriers, markers and controls.

29. A kit comprising the expression vector of claim 12, and optionally further comprises one or more auxiliary agents, wherein the auxiliary agents are solvents, buffers, carriers, markers and controls.

30. A kit comprising the host cell of claim 13, and optionally further comprises one or more auxiliary agents, wherein the auxiliary agents are solvents, buffers, carriers, markers and controls.

31. A kit comprising the expression vector of claim 26, and optionally further comprises one or more auxiliary agents, wherein the auxiliary agents are solvents, buffers, carriers, markers and controls.

32. A kit comprising the host cell of claim 27, and optionally further comprises one or more auxiliary agents, wherein the auxiliary agents are solvents, buffers, carriers, markers and controls.

33. A pharmaceutical composition containing a parvovirus according to claim 2.

\* \* \* \* \*

```
                    SEQUENCE LISTING

<160> NUMBER OF SEQ ID NOS: 16

<210> SEQ ID NO 1
<211> LENGTH: 110
<212> TYPE: DNA
<213> ORGANISM: Artificial Sequence
<220> FEATURE:
<223> OTHER INFORMATION: Genetic variation of hgH1-PV: synthetic
      construct

<400> SEQUENCE: 1
gcacaccaaa tactcctgtt gcgggcactg cagcaagcca aaacactggg gaggctggtt     60
ccacagcctg ccaaggtgct caacggagcc caacctggtc cgagatcgag               110

<210> SEQ ID NO 2
<211> LENGTH: 150
<212> TYPE: DNA
<213> ORGANISM: Artificial Sequence
<220> FEATURE:
<223> OTHER INFORMATION: Genetic variation of H1-PV: synthetic construct

<400> SEQUENCE: 2
ctctgactcc gagaagtacg cctctcagcc aaaactacgc tcttactcca cttgcatcgg     60
accttgcgga cctagctcta gagccttgga gcacaccaaa tactcctgtt gcgggcactg    120
cagcaagcca aaacactggg gaggctggtt                                     150

<210> SEQ ID NO 3
<211> LENGTH: 20
<212> TYPE: DNA
<213> ORGANISM: Artificial Sequence
<220> FEATURE:
<223> OTHER INFORMATION: Genetic variation of H1-PV: synthetic construct

<400> SEQUENCE: 3
gctggcgagg actatgatgc                                                 20

<210> SEQ ID NO 4
<211> LENGTH: 20
<212> TYPE: DNA
<213> ORGANISM: Artificial Sequence
<220> FEATURE:
```

```
<223> OTHER INFORMATION: Genetic variation of H1-PV: synthetic construct

<400> SEQUENCE: 4
acaacatggc gaaaattggg                                                   20

<210> SEQ ID NO 5
<211> LENGTH: 20
<212> TYPE: DNA
<213> ORGANISM: Artificial Sequence
<220> FEATURE:
<223> OTHER INFORMATION: Genetic variation of H1-PV: synthetic construct

<400> SEQUENCE: 5
gcgagaaaac gccatagctg                                                   20

<210> SEQ ID NO 6
<211> LENGTH: 19
<212> TYPE: DNA
<213> ORGANISM: Artificial Sequence
<220> FEATURE:
<223> OTHER INFORMATION: Genetic variation of H1-PV: synthetic construct

<400> SEQUENCE: 6
tataaaaata acataatat                                                    19

<210> SEQ ID NO 7
<211> LENGTH: 22
<212> TYPE: DNA
<213> ORGANISM: Artificial Sequence
<220> FEATURE:
<223> OTHER INFORMATION: Genetic variation of H1-PV: synthetic construct

<400> SEQUENCE: 7
aacataatat ggtattggtt aa                                                22

<210> SEQ ID NO 8
<211> LENGTH: 20
<212> TYPE: DNA
<213> ORGANISM: Artificial Sequence
<220> FEATURE:
<223> OTHER INFORMATION: Genetic variation of H1-PV: synthetic construct

<400> SEQUENCE: 8
ctgtaaaaaa caatagaact                                                   20

<210> SEQ ID NO 9
<211> LENGTH: 71
<212> TYPE: DNA
<213> ORGANISM: Artificial Sequence
<220> FEATURE:
<223> OTHER INFORMATION: Genetic variation of H1-PV: synthetic construct

<400> SEQUENCE: 9
atataagaag attttgtatt ttaaaataaa tatagttagt tggttaatgt tagatagaat       60
ataaaaagat t                                                            71

<210> SEQ ID NO 10
<211> LENGTH: 672
<212> TYPE: PRT
<213> ORGANISM: Artificial Sequence
<220> FEATURE:
<223> OTHER INFORMATION: Variations in NS1 of H1-PV: synthetic construct

<400> SEQUENCE: 10

Met Ala Gly Asn Ala Tyr Ser Asp Glu Val Leu Gly Val Thr Asn Trp
```

```
  1               5                  10                 15
Leu Lys Asp Lys Ser Ser Gln Glu Val Phe Ser Phe Val Phe Lys Asn
             20                 25                 30

Glu Asn Val Gln Leu Asn Gly Lys Asp Ile Gly Trp Asn Ser Tyr Arg
             35                 40                 45

Lys Glu Leu Gln Asp Asp Glu Leu Lys Ser Leu Gln Arg Gly Ala Glu
             50                 55                 60

Thr Thr Trp Asp Gln Ser Glu Asp Met Glu Trp Glu Ser Ala Val Asp
 65                 70                 75                 80

Asp Met Thr Lys Lys Gln Val Phe Ile Phe Asp Ser Leu Val Lys Lys
                 85                 90                 95

Cys Leu Phe Glu Val Leu Ser Thr Lys Asn Ile Ala Pro Ser Asn Val
            100                105                110

Thr Trp Phe Val Gln His Glu Trp Gly Lys Asp Pro Gly Trp His Cys
            115                120                125

His Val Leu Ile Gly Gly Lys Asp Phe Ser Gln Pro Gln Gly Lys Trp
            130                135                140

Trp Arg Arg Gln Leu Asn Val Tyr Trp Ser Arg Trp Leu Val Thr Ala
145                150                155                160

Cys Asn Val Gln Leu Thr Pro Ala Glu Arg Ile Lys Leu Arg Glu Ile
                165                170                175

Ala Glu Asp Ser Glu Trp Val Thr Leu Leu Thr Tyr Lys His Lys His
                180                185                190

Thr Lys Lys Asp Tyr Thr Lys Cys Val Leu Phe Gly Asn Met Ile Ala
                195                200                205

Tyr Tyr Phe Leu Ser Lys Lys Ile Cys Thr Ser Pro Pro Arg Asp
210                215                220

Gly Gly Tyr Phe Leu Ser Ser Asp Ser Gly Trp Lys Thr Asn Phe Leu
225                230                235                240

Lys Glu Gly Glu Arg His Leu Val Ser Lys Leu Tyr Thr Asp Glu Met
                245                250                255

Lys Pro Glu Thr Val Glu Thr Val Thr Thr Ala Gln Glu Ala Lys
                260                265                270

Arg Gly Arg Ile Gln Thr Arg Glu Glu Val Ser Ile Lys Thr Thr Leu
                275                280                285

Lys Glu Leu Val His Lys Arg Val Thr Ser Pro Glu Asp Trp Met Met
                290                295                300

Met Gln Pro Asp Ser Tyr Ile Glu Met Met Ala Gln Pro Gly Gly Glu
305                310                315                320

Asn Leu Leu Lys Asn Thr Leu Glu Ile Cys Thr Leu Thr Leu Ala Arg
                325                330                335

Thr Lys Thr Ala Phe Asp Leu Ile Leu Glu Lys Ala Glu Thr Ser Lys
                340                345                350

Leu Ala Asn Phe Ser Met Ala Ser Thr Arg Thr Cys Arg Ile Phe Ala
                355                360                365

Glu His Gly Trp Asn Tyr Ile Lys Val Cys His Ala Ile Cys Cys Val
                370                375                380

Leu Asn Arg Gln Gly Gly Lys Arg Asn Thr Val Leu Phe His Gly Pro
385                390                395                400

Ala Ser Thr Gly Lys Ser Ile Ile Ala Gln Ala Ile Ala Gln Ala Val
                405                410                415

Gly Asn Val Gly Cys Tyr Asn Ala Ala Asn Val Asn Phe Pro Phe Asn
                420                425                430
```

-continued

```
Asp Cys Thr Asn Lys Asn Leu Ile Trp Val Glu Glu Ala Gly Asn Phe
            435                 440                 445

Gly Gln Gln Val Asn Gln Phe Lys Ala Ile Cys Ser Gly Gln Thr Ile
        450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Arg Ile Gly Cys
                485                 490                 495

Glu Glu Arg Pro Glu His Thr Gln Pro Ile Arg Asp Arg Met Leu Asn
                500                 505                 510

Ile His Leu Thr Arg Thr Leu Pro Gly Asp Phe Gly Leu Val Asp Lys
            515                 520                 525

His Glu Trp Pro Leu Ile Cys Ala Trp Leu Val Lys Asn Gly Tyr Gln
            530                 535                 540

Ser Thr Met Ala Cys Tyr Cys Ala Lys Trp Gly Lys Val Pro Asp Trp
545                 550                 555                 560

Ser Glu Asp Trp Ala Glu Pro Lys Leu Asp Thr Pro Ile Asn Ser Leu
                565                 570                 575

Gly Ser Met Arg Ser Pro Ser Leu Thr Pro Arg Ser Thr Pro Leu Ser
                580                 585                 590

Gln Asn Tyr Ala Leu Thr Pro Leu Ala Ser Asp Leu Ala Asp Leu Ala
            595                 600                 605

Leu Glu Pro Trp Ser Thr Pro Asn Thr Pro Val Ala Gly Thr Ala Ala
            610                 615                 620

Ser Gln Asn Thr Gly Glu Ala Gly Ser Thr Ala Cys Gln Gly Ala Gln
625                 630                 635                 640

Arg Ser Pro Thr Trp Ser Glu Ile Glu Ala Asp Leu Arg Ala Cys Phe
                645                 650                 655

Ser Gln Glu Gln Leu Glu Ser Asp Phe Asn Glu Glu Leu Thr Leu Asp
                660                 665                 670

<210> SEQ ID NO 11
<211> LENGTH: 199
<212> TYPE: PRT
<213> ORGANISM: Artificial Sequence
<220> FEATURE:
<223> OTHER INFORMATION: Variations in NS2 of H1-PV: synthetic construct

<400> SEQUENCE: 11

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
            20                  25                  30

Glu Asn Val Gln Leu Asn Gly Lys Asp Ile Gly Trp Asn Ser Tyr Arg
        35                  40                  45

Lys Glu Leu Gln Asp Asp Glu Leu Lys Ser Leu Gln Arg Gly Ala Glu
    50                  55                  60

Thr Thr Trp Asp Gln Ser Glu Asp Met Glu Trp Glu Ser Ala Val Asp
65                  70                  75                  80

Met Thr Lys Lys Phe Asn Ala Leu Thr Ile Ser Asp Ser Glu Lys Tyr
                85                  90                  95

Ala Ser Gln Pro Lys Leu Arg Ser Tyr Ser Thr Cys Ile Gly Pro Cys
            100                 105                 110

Gly Pro Ser Ser Arg Ala Leu Glu His Thr Lys Tyr Ser Cys Cys Gly
            115                 120                 125
```

```
His Cys Ser Lys Pro Lys His Trp Gly Gly Trp Phe His Ser Leu Pro
    130                 135                 140

Arg Cys Ser Thr Glu Pro Asn Leu Val Arg Asp Arg Gly Gly Phe Glu
145                 150                 155                 160

Ser Leu Leu Gln Ser Arg Thr Val Gly Glu Arg Leu Gln Arg Gly Ala
                165                 170                 175

Asp Leu Gly Leu Arg Tyr Gly Val Leu Met Tyr Asp Tyr Leu Phe Tyr
            180                 185                 190

Arg Pro Glu Ile Thr Trp Phe
        195

<210> SEQ ID NO 12
<211> LENGTH: 738
<212> TYPE: PRT
<213> ORGANISM: Artificial Sequence
<220> FEATURE:
<223> OTHER INFORMATION: Variations in VP1/2 of H1-PV: synthetic
      construct

<400> SEQUENCE: 12

Met Ala Pro Pro Ala Lys Arg Ala Lys Arg Gly Trp Val Pro Pro Gly
1               5                   10                  15

Tyr Lys Tyr Leu Gly Pro Gly Asn Ser Leu Asp Gln Gly Glu Pro Thr
            20                  25                  30

Asn Pro Ser Asp Ala Ala Ala Lys Glu His Asp Glu Ala Tyr Asp Gln
        35                  40                  45

Tyr Ile Lys Ser Gly Lys Asn Pro Tyr Leu Tyr Phe Ser Pro Ala Asp
    50                  55                  60

Gln Arg Phe Ile Asp Gln Thr Lys Asp Ala Lys Asp Trp Gly Gly Lys
65                  70                  75                  80

Val Gly His Tyr Phe Phe Arg Thr Lys Arg Ala Phe Ala Pro Lys Leu
                85                  90                  95

Ser Thr Asp Ser Glu Pro Gly Thr Ser Gly Thr Ser Gly Val Ser Arg
            100                 105                 110

Pro Gly Lys Arg Thr Lys Pro Pro Ala His Ile Phe Val Asn Gln Ala
        115                 120                 125

Arg Ala Lys Lys Lys Arg Ala Ser Leu Ala Ala Gln Gln Arg Thr Leu
    130                 135                 140

Thr Met Ser Asp Gly Thr Glu Thr Asn Gln Pro Asp Thr Gly Ile Ala
145                 150                 155                 160

Asn Ala Arg Val Glu Arg Ser Ala Asp Gly Gly Gly Ser Ser Gly Gly
                165                 170                 175

Gly Gly Gly Ser Gly Gly Gly Gly Ile Gly Val Ser Thr Gly Thr Tyr
            180                 185                 190

Asp Asn Gln Thr Thr Tyr Lys Phe Leu Gly Asp Gly Trp Val Glu Ile
        195                 200                 205

Thr Ala His Ala Ser Arg Leu Leu His Leu Gly Met Pro Pro Ser Glu
    210                 215                 220

Asn Tyr Cys Arg Val Thr Val His Asn Asn Gln Thr Thr Gly His Gly
225                 230                 235                 240

Thr Lys Val Lys Gly Asn Met Ala Tyr Asp Thr His Gln Gln Ile Trp
                245                 250                 255

Thr Pro Trp Ser Leu Val Asp Ala Asn Ala Trp Gly Val Trp Phe Gln
            260                 265                 270

Pro Ser Asp Trp Gln Phe Ile Gln Asn Ser Met Glu Ser Leu Asn Leu
```

-continued

```
                275                 280                 285
Asp Ser Leu Ser Gln Glu Leu Phe Asn Val Val Lys Thr Val Thr
290                 295                 300
Glu Gln Gln Gly Ala Gly Gln Asp Ala Ile Lys Val Tyr Asn Asn Asp
305                 310                 315                 320
Leu Thr Ala Cys Met Met Val Ala Leu Asp Ser Asn Asn Ile Leu Pro
                325                 330                 335
Tyr Thr Pro Ala Ala Gln Thr Ser Glu Thr Leu Gly Phe Tyr Pro Trp
                340                 345                 350
Lys Pro Thr Ala Pro Ala Pro Tyr Arg Tyr Phe Phe Met Pro Arg
                355                 360                 365
Gln Leu Ser Val Thr Ser Ser Asn Ser Ala Glu Gly Thr Gln Ile Thr
370                 375                 380
Asp Thr Ile Gly Glu Pro Gln Ala Leu Asn Ser Gln Phe Phe Thr Ile
385                 390                 395                 400
Glu Asn Thr Leu Pro Ile Thr Leu Leu Arg Thr Gly Asp Glu Phe Thr
                405                 410                 415
Thr Gly Thr Tyr Ile Phe Asn Thr Asp Pro Leu Lys Leu Thr His Thr
                420                 425                 430
Trp Gln Thr Asn Arg His Leu Ala Cys Leu Gln Gly Ile Thr Asp Leu
                435                 440                 445
Pro Thr Ser Asp Thr Ala Thr Ala Ser Leu Thr Ala Asn Gly Asp Arg
450                 455                 460
Phe Gly Ser Thr Gln Thr Gln Asn Val Asn Tyr Val Thr Glu Ala Leu
465                 470                 475                 480
Arg Thr Arg Pro Ala Gln Ile Gly Phe Met Gln Pro His Asp Asn Phe
                485                 490                 495
Glu Ala Asn Arg Gly Gly Pro Phe Lys Val Pro Val Val Pro Leu Asp
                500                 505                 510
Ile Thr Ala Gly Glu Asp His Asp Ala Asn Gly Ala Ile Arg Phe Asn
                515                 520                 525
Tyr Gly Lys Gln His Gly Glu Asp Trp Ala Lys Gln Gly Ala Ala Pro
                530                 535                 540
Glu Arg Tyr Thr Trp Asp Ala Ile Asp Ser Ala Ala Gly Arg Asp Thr
545                 550                 555                 560
Ala Arg Cys Phe Val Gln Ser Ala Pro Ile Ser Ile Pro Pro Asn Gln
                565                 570                 575
Asn Gln Ile Leu Gln Arg Glu Asp Ala Ile Ala Gly Arg Thr Asn Met
                580                 585                 590
His Tyr Thr Asn Val Phe Asn Ser Tyr Gly Pro Leu Ser Ala Phe Pro
                595                 600                 605
His Pro Asp Pro Ile Tyr Pro Asn Gly Gln Ile Trp Asp Lys Glu Leu
                610                 615                 620
Asp Leu Glu His Lys Pro Arg Leu His Val Thr Ala Pro Phe Val Cys
625                 630                 635                 640
Lys Asn Asn Pro Pro Gly Gln Leu Phe Val His Leu Gly Pro Asn Leu
                645                 650                 655
Thr Asp Gln Phe Asp Pro Asn Ser Thr Thr Val Ser Arg Ile Val Thr
                660                 665                 670
Tyr Ser Thr Phe Tyr Trp Lys Gly Ile Leu Lys Phe Lys Ala Lys Leu
                675                 680                 685
Arg Pro Asn Leu Thr Trp Asn Pro Val Tyr Gln Ala Thr Thr Asp Ser
690                 695                 700
```

```
Val Ala Asn Ser Tyr Met Asn Val Lys Lys Trp Leu Pro Ser Ala Thr
705                 710                 715                 720

Gly Asn Met His Ser Asp Pro Leu Ile Cys Arg Pro Val Pro His Met
                725                 730                 735

Thr Tyr

<210> SEQ ID NO 13
<211> LENGTH: 5
<212> TYPE: PRT
<213> ORGANISM: Artificial Sequence
<220> FEATURE:
<223> OTHER INFORMATION: Synthetic construct

<400> SEQUENCE: 13

Gly Met Pro Pro Arg
1               5

<210> SEQ ID NO 14
<211> LENGTH: 672
<212> TYPE: PRT
<213> ORGANISM: Artificial Sequence
<220> FEATURE:
<223> OTHER INFORMATION: NS1 of plaque 13: synthetic construct

<400> SEQUENCE: 14

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
                20                  25                  30

Glu Asn Val Gln Leu Asn Gly Lys Asp Ile Gly Trp Asn Ser Tyr Arg
            35                  40                  45

Lys Glu Leu Gln Asp Asp Glu Leu Lys Ser Leu Gln Arg Gly Ala Glu
        50                  55                  60

Thr Thr Trp Asp Gln Ser Glu Asp Met Glu Trp Glu Ser Ala Val Asp
65                  70                  75                  80

Asp Met Thr Lys Lys Gln Val Phe Ile Phe Asp Ser Leu Val Lys Lys
                85                  90                  95

Cys Leu Phe Glu Val Leu Ser Thr Lys Asn Ile Ala Pro Ser Asn Val
                100                 105                 110

Thr Trp Phe Val Gln His Glu Trp Gly Lys Asp Pro Gly Trp His Cys
            115                 120                 125

His Val Leu Ile Gly Gly Lys Asp Phe Ser Gln Pro Gln Gly Lys Trp
        130                 135                 140

Trp Arg Arg Gln Leu Asn Val Tyr Trp Ser Arg Trp Leu Val Thr Ala
145                 150                 155                 160

Cys Asn Val Gln Leu Thr Pro Ala Glu Arg Ile Lys Leu Arg Glu Ile
                165                 170                 175

Ala Glu Asp Ser Glu Trp Val Thr Leu Leu Thr Tyr Lys His Lys His
            180                 185                 190

Thr Lys Lys Asp Tyr Thr Lys Cys Val Leu Phe Gly Asn Met Ile Ala
        195                 200                 205

Tyr Tyr Phe Leu Ser Lys Lys Ile Cys Thr Ser Pro Pro Arg Asp
210                 215                 220

Gly Gly Tyr Phe Leu Ser Ser Asp Ser Gly Trp Lys Thr Asn Phe Leu
225                 230                 235                 240

Lys Glu Gly Glu Arg His Leu Val Ser Lys Leu Tyr Thr Asp Glu Met
                245                 250                 255
```

```
Lys Pro Glu Thr Val Glu Thr Val Thr Ala Gln Glu Ala Lys
            260                 265                 270

Arg Gly Arg Ile Gln Thr Arg Glu Val Ser Ile Lys Thr Thr Leu
        275                 280                 285

Lys Glu Leu Val His Lys Arg Val Thr Ser Pro Glu Asp Trp Met Met
290                 295                 300

Met Gln Pro Asp Ser Tyr Ile Glu Met Met Ala Gln Pro Gly Gly Glu
305                 310                 315                 320

Asn Leu Leu Lys Asn Thr Leu Glu Ile Cys Thr Leu Thr Leu Ala Arg
                325                 330                 335

Thr Lys Thr Ala Phe Asp Leu Ile Leu Glu Lys Ala Glu Thr Ser Lys
            340                 345                 350

Leu Ala Asn Phe Ser Met Ala Ser Thr Arg Thr Cys Arg Ile Phe Ala
        355                 360                 365

Glu His Gly Trp Asn Tyr Ile Lys Val Cys His Ala Ile Cys Cys Val
370                 375                 380

Leu Asn Arg Gln Gly Gly Lys Arg Asn Thr Val Leu Phe His Gly Pro
385                 390                 395                 400

Ala Ser Thr Gly Lys Ser Ile Ile Ala Gln Ala Ile Ala Gln Ala Val
                405                 410                 415

Gly Asn Val Gly Cys Tyr Asn Ala Ala Asn Val Asn Phe Pro Phe Asn
            420                 425                 430

Asp Cys Thr Asn Lys Asn Leu Ile Trp Val Glu Glu Ala Gly Asn Phe
        435                 440                 445

Gly Gln Gln Val Asn Gln Phe Lys Ala Ile Cys Ser Gly Gln Thr Ile
450                 455                 460

Arg Ile Asp Gln Lys Gly Lys Gly Ser Lys Gln Ile Glu Pro Thr Pro
465                 470                 475                 480

Val Ile Met Thr Thr Asn Glu Asn Ile Thr Val Val Arg Ile Gly Cys
                485                 490                 495

Glu Glu Arg Pro Glu His Thr Gln Pro Ile Arg Asp Arg Met Leu Asn
            500                 505                 510

Ile His Leu Thr Arg Thr Leu Pro Gly Asp Phe Gly Leu Val Asp Lys
        515                 520                 525

His Glu Trp Pro Leu Ile Cys Ala Trp Leu Val Lys Asn Gly Tyr Gln
530                 535                 540

Ser Thr Met Ala Cys Tyr Cys Ala Lys Trp Gly Lys Val Pro Asp Trp
545                 550                 555                 560

Ser Glu Asp Trp Ala Glu Pro Lys Leu Asp Thr Pro Ile Asn Ser Leu
                565                 570                 575

Gly Ser Met Arg Ser Pro Ser Leu Thr Pro Arg Ser Thr Pro Leu Ser
            580                 585                 590

Gln Asn Tyr Ala Leu Thr Pro Leu Ala Ser Asp Leu Ala Asp Leu Ala
        595                 600                 605

Leu Glu Pro Trp Ser Thr Pro Asn Thr Pro Val Ala Gly Thr Ala Ala
610                 615                 620

Ser Gln Asn Thr Gly Glu Ala Gly Ser Thr Ala Cys Gln Gly Ala Gln
625                 630                 635                 640

Arg Ser Pro Thr Trp Ser Glu Ile Glu Ala Asp Leu Arg Ala Cys Phe
                645                 650                 655

Ser Gln Glu Gln Leu Glu Ser Asp Phe Asn Glu Glu Leu Thr Leu Asp
            660                 665                 670
```

-continued

```
<210> SEQ ID NO 15
<211> LENGTH: 199
<212> TYPE: PRT
<213> ORGANISM: Artificial Sequence
<220> FEATURE:
<223> OTHER INFORMATION: NS2 of plaque 13: synthetic construct

<400> SEQUENCE: 15

Met Ala Gly Asn Ala Tyr Ser Asp Glu Val Leu Gly Val Thr Asn Trp
1               5                   10                  15

Leu Lys Asp Lys Ser Ser Gln Glu Val Phe Ser Phe Val Phe Lys Asn
            20                  25                  30

Glu Asn Val Gln Leu Asn Gly Lys Asp Ile Gly Trp Asn Ser Tyr Arg
        35                  40                  45

Lys Glu Leu Gln Asp Asp Glu Leu Lys Ser Leu Gln Arg Gly Ala Glu
    50                  55                  60

Thr Thr Trp Asp Gln Ser Glu Asp Met Glu Trp Glu Ser Ala Val Asp
65                  70                  75                  80

Met Thr Lys Lys Phe Asn Ala Leu Thr Ile Ser Asp Ser Glu Lys Tyr
                85                  90                  95

Ala Ser Gln Pro Lys Leu Arg Ser Tyr Ser Thr Cys Ile Gly Pro Cys
            100                 105                 110

Gly Pro Ser Ser Arg Ala Leu Glu His Thr Lys Tyr Ser Cys Cys Gly
        115                 120                 125

His Cys Ser Lys Pro Lys His Trp Gly Gly Trp Phe His Ser Leu Pro
    130                 135                 140

Arg Cys Ser Thr Glu Pro Asn Leu Val Arg Asp Arg Gly Gly Phe Glu
145                 150                 155                 160

Ser Leu Leu Gln Ser Arg Thr Val Gly Glu Arg Leu Gln Arg Gly Ala
                165                 170                 175

Asp Leu Gly Leu Arg Tyr Gly Val Leu Met Tyr Asp Tyr Leu Phe Tyr
            180                 185                 190

Arg Pro Glu Ile Thr Trp Phe
        195

<210> SEQ ID NO 16
<211> LENGTH: 738
<212> TYPE: PRT
<213> ORGANISM: Artificial Sequence
<220> FEATURE:
<223> OTHER INFORMATION: VP1/2 of plaque 13: synthetic construct

<400> SEQUENCE: 16

Met Ala Pro Pro Ala Lys Arg Ala Lys Arg Gly Trp Val Pro Pro Gly
1               5                   10                  15

Tyr Lys Tyr Leu Gly Pro Gly Asn Ser Leu Asp Gln Gly Glu Pro Thr
            20                  25                  30

Asn Pro Ser Asp Ala Ala Ala Lys Glu His Asp Glu Ala Tyr Asp Gln
        35                  40                  45

Tyr Ile Lys Ser Gly Lys Asn Pro Tyr Leu Tyr Phe Ser Pro Ala Asp
    50                  55                  60

Gln Arg Phe Ile Asp Gln Thr Lys Asp Ala Lys Asp Trp Gly Gly Lys
65                  70                  75                  80

Val Gly His Tyr Phe Phe Arg Thr Lys Arg Ala Phe Ala Pro Lys Leu
                85                  90                  95

Ser Thr Asp Ser Glu Pro Gly Thr Ser Gly Thr Ser Gly Val Ser Arg
            100                 105                 110
```

```
Pro Gly Lys Arg Thr Lys Pro Pro Ala His Ile Phe Val Asn Gln Ala
            115                 120                 125
Arg Ala Lys Lys Lys Arg Ala Ser Leu Ala Ala Gln Gln Arg Thr Leu
    130                 135                 140
Thr Met Ser Asp Gly Thr Glu Thr Asn Gln Pro Asp Thr Gly Ile Ala
145                 150                 155                 160
Asn Ala Arg Val Glu Arg Ser Ala Asp Gly Gly Ser Ser Gly Gly Gly
                165                 170                 175
Gly Gly Gly Ser Gly Gly Gly Ile Gly Val Ser Thr Gly Thr Tyr
            180                 185                 190
Asp Asn Gln Thr Thr Tyr Lys Phe Leu Gly Asp Gly Trp Val Glu Ile
            195                 200                 205
Thr Ala His Ala Ser Arg Leu Leu His Leu Gly Met Pro Pro Ser Glu
    210                 215                 220
Asn Tyr Cys Arg Val Thr Val His Asn Asn Gln Thr Thr Gly His Gly
225                 230                 235                 240
Thr Lys Val Lys Gly Asn Met Ala Tyr Asp Thr His Gln Gln Ile Trp
                245                 250                 255
Thr Pro Trp Ser Leu Val Asp Ala Asn Ala Trp Gly Val Trp Phe Gln
            260                 265                 270
Pro Ser Asp Trp Gln Phe Ile Gln Asn Ser Met Glu Ser Leu Asn Leu
        275                 280                 285
Asp Ser Leu Ser Gln Glu Leu Phe Asn Val Val Lys Thr Val Thr
    290                 295                 300
Glu Gln Gln Gly Ala Gly Gln Asp Ala Ile Lys Val Tyr Asn Asn Asp
305                 310                 315                 320
Leu Thr Ala Cys Met Met Val Ala Leu Asp Ser Asn Asn Ile Leu Pro
                325                 330                 335
Tyr Thr Pro Ala Ala Gln Thr Ser Glu Thr Leu Gly Phe Tyr Pro Trp
            340                 345                 350
Lys Pro Thr Ala Pro Ala Pro Tyr Arg Tyr Tyr Phe Phe Met Pro Arg
        355                 360                 365
Gln Leu Ser Val Thr Ser Ser Asn Ser Ala Glu Gly Thr Gln Ile Thr
    370                 375                 380
Asp Thr Ile Gly Glu Pro Gln Ala Leu Asn Ser Gln Phe Phe Thr Ile
385                 390                 395                 400
Glu Asn Thr Leu Pro Ile Thr Leu Leu Arg Thr Gly Asp Glu Phe Thr
                405                 410                 415
Thr Gly Thr Tyr Ile Phe Asn Thr Asp Pro Leu Lys Leu Thr His Thr
            420                 425                 430
Trp Gln Thr Asn Arg His Leu Ala Cys Leu Gln Gly Ile Thr Asp Leu
        435                 440                 445
Pro Thr Ser Asp Thr Ala Thr Ala Ser Leu Thr Ala Asn Gly Asp Arg
    450                 455                 460
Phe Gly Ser Thr Gln Thr Gln Asn Val Asn Tyr Val Thr Glu Ala Leu
465                 470                 475                 480
Arg Thr Arg Pro Ala Gln Ile Gly Phe Met Gln Pro His Asp Asn Phe
                485                 490                 495
Glu Ala Asn Arg Gly Gly Pro Phe Lys Val Pro Val Val Pro Leu Asp
            500                 505                 510
Ile Thr Ala Gly Glu Asp His Asp Ala Asn Gly Ala Ile Arg Phe Asn
        515                 520                 525
```

```
Tyr Gly Lys Gln His Gly Glu Asp Trp Ala Lys Gln Gly Ala Ala Pro
    530             535                 540

Glu Arg Tyr Thr Trp Asp Ala Ile Asp Ser Ala Ala Gly Arg Asp Thr
545             550                 555                 560

Ala Arg Cys Phe Val Gln Ser Ala Pro Ile Ser Ile Pro Pro Asn Gln
            565                 570                 575

Asn Gln Ile Leu Gln Arg Glu Asp Ala Ile Ala Gly Arg Thr Asn Met
            580                 585                 590

His Tyr Thr Asn Val Phe Asn Ser Tyr Gly Pro Leu Ser Ala Phe Pro
        595                 600                 605

His Pro Asp Pro Ile Tyr Pro Asn Gly Gln Ile Trp Asp Lys Glu Leu
    610                 615                 620

Asp Leu Glu His Lys Pro Arg Leu His Val Thr Ala Pro Phe Val Cys
625             630                 635                 640

Lys Asn Asn Pro Pro Gly Gln Leu Phe Val His Leu Gly Pro Asn Leu
            645                 650                 655

Thr Asp Gln Phe Asp Pro Asn Ser Thr Thr Val Ser Arg Ile Val Thr
            660                 665                 670

Tyr Ser Thr Phe Tyr Trp Lys Gly Ile Leu Lys Phe Lys Ala Lys Leu
        675                 680                 685

Arg Pro Asn Leu Thr Trp Asn Pro Val Tyr Gln Ala Thr Thr Asp Ser
    690                 695                 700

Val Ala Asn Ser Tyr Met Asn Val Lys Lys Trp Leu Pro Ser Ala Thr
705             710                 715                 720

Gly Asn Met His Ser Asp Pro Leu Ile Cys Arg Pro Val Pro His Met
            725                 730                 735

Thr Tyr
```